(12) United States Patent
Frewen et al.

(10) Patent No.: US 11,151,497 B2
(45) Date of Patent: Oct. 19, 2021

(54) MICROBIAL STRAIN DESIGN SYSTEM AND METHODS FOR IMPROVED LARGE-SCALE PRODUCTION OF ENGINEERED NUCLEOTIDE SEQUENCES

(71) Applicant: Zymergen, Inc., Emeryville, CA (US)

(72) Inventors: Barbara Frewen, Alameda, CA (US); Aaron Kimball, San Francisco, CA (US)

(73) Assignee: Zymergen Inc., Emeryville, CA (US)

( * ) Notice: Subject to any disclaimer, the term of this patent is extended or adjusted under 35 U.S.C. 154(b) by 676 days.

(21) Appl. No.: 15/140,296

(22) Filed: Apr. 27, 2016

(65) Prior Publication Data

US 2017/0316353 A1    Nov. 2, 2017

(51) Int. Cl.

| | | |
|---|---|---|
| *G06Q 10/06* | (2012.01) | |
| *G16B 50/00* | (2019.01) | |
| *G05B 15/00* | (2006.01) | |
| *G16B 99/00* | (2019.01) | |
| *G16B 50/30* | (2019.01) | |
| *G16B 35/10* | (2019.01) | |

(52) U.S. Cl.
CPC ......... *G06Q 10/0633* (2013.01); *G05B 15/00* (2013.01); *G06Q 10/0631* (2013.01); *G16B 35/10* (2019.02); *G16B 50/00* (2019.02); *G16B 50/30* (2019.02); *G16B 99/00* (2019.02)

(58) Field of Classification Search
None
See application file for complete search history.

(56) References Cited

U.S. PATENT DOCUMENTS

| | | | |
|---|---|---|---|
| 7,208,278 | B2 | 4/2007 | Chen et al. |
| 7,826,975 | B2 | 11/2010 | Maranas |
| 8,108,152 | B2 | 1/2012 | Maranas |
| 8,332,160 | B1 † | 12/2012 | Platt |
| 2011/0054654 | A1 | 3/2011 | Phillips et al. |
| 2016/0246923 | A1 | 8/2016 | Rooyen et al. |

FOREIGN PATENT DOCUMENTS

| | | |
|---|---|---|
| CN | 104651491 A | 5/2015 |
| CN | 104661737 A | 5/2015 |
| JP | 2002318992 | 10/2002 |
| JP | 2003536117 A | 12/2003 |

OTHER PUBLICATIONS

"Designing a Million Genomes: Machine Learning, Automation and Biotech.", Strata + Hadoop World, Make Data Work conference, London, UK, May 5, 2015; https://youtu.be/658kvYgrJBE, Published on Oct. 7, 2015, Business-focused talk at Strata UK 2015 by Aaron Kimball, CTO of Zymergen Inc.

ABI 3900 High Throughput DNA Synthesizer, User's Manual, 2001, 144 pages, Applied Biosystems, US (retrieved on Mar. 16, 2018 from URL cited in Written Opinion).

Alter, et al., Singular value decomposition for genome-wide expression data processing and modeling, PNAS, Aug. 20, 2000, pp. 10101-10106, v. 97, No. 18.

Darter, et al., Prediction of phenotype and gene expression for combinations of mutations, Molecular Systems Biology 3:96, 2007, 9 pages.

Giaever, et al., Functional profiling of the *Saccharomyces cerevisiae* genome, Nature, Jul. 25, 2002, pp. 387-391, v. 418, Nature Publishing Group.

Lewis et al., Constraining the metabolic genotype-phenotype relationship using a phylogeny of in silico methods, Nature Reviews, Microbiology, Apr. 2012, pp. 291-305, v. 10, MacMillan Publishers Limited.

Szappanos, et al., "An integrated approach to characterize genetic interaction networks in yeast metabolism". Nature Genetics (May 29, 2011); 43(7): 656-662.

"Designing a Million Genomes: Machine Learning, Automation and Biotech.", Strata + Hadoop World, Make Data Work conference, London, UK, May 5, 2015; https://youtu.be/658kvYgrJBE, Published on Oct 7, 2015, Business-focused talk at Strata UK 2015 by Aaron IGmball, CTO of Zymergen Inc.

"The Data-Driven future of biotechnology." https://www.youtube.com/watch?v=IYmgJUHcG9g&feature=youtu.be&t=915, Strata + Hadoop World, NY Sep. 28-Oct. 1, 2015, Published on Nov. 15, 2015, Technical talk at Strata NY 2015 by Aaron Kimball, CTO of Zymergen Inc. about Zymergen's technology.

Bartley et al., "Synthetic biology open language (SBOL) version 2.0.0," Journal of Integrative Bioinformatics (JIB) (2015); 12(2): 902-991.

(Continued)

*Primary Examiner* — Joseph Woitach
(74) *Attorney, Agent, or Firm* — Almanac IP Advisors LLP

(57) ABSTRACT

The generation of a factory order to control production of nucleotide sequences by a gene manufacturing system includes receiving an expression indicating an operation on sequence operands, each representing at least one nucleotide sequence part, evaluating the expression to a sequence specification, wherein the sequence specification comprises a data structure including one or more first-level operations and one or more second-level operations, and generating the factory order based upon execution of the one or more first-level operations and the one or more second-level operations. In a recursive manner, the one or more first-level operations operate on at least one first-level sequence operand, the value of which is resolved by execution of one or more of the second-level operations. The factory order may then be provided to the gene manufacturing system to assemble the sequence parts into nucleotide sequences represented by the sequence specification.

81 Claims, 7 Drawing Sheets
Specification includes a Sequence Listing.

(56) References Cited

OTHER PUBLICATIONS

Bilitchenko et al., "Eugene—a domain specific language for specifying and constraining synthetic biological parts, devices, and systems." PloS ONE (2011); 6.4: e18882 (and Supplemental Data).
Chen et al., "DeviceEditor visual biological CAD canvas." Journal of Biological Engineering (2012); 6:1, pp. 1-12.
Frewen et al., "A Detailed, flexible model for sharing DNA concepts." IWBDA 2015, 7th International Workshop on Bio-Design Automation, University of Washington, pp. 66-67, Aug. 19-21, 2015 (Presentation and Poster), 86 pages.
Hillson, "j5 DNA Assembly Design Automation Software." ACS Synthetic Biology (2011); 1:14-21.
i5 DeviceEditor manual excerpt from https://j5.jbei.org/index.php/Main_Page_downloadedcontent available Apr. 19, 2016, 45 pages.
Kimball, A., "The Data-Driven Future of Biotechnology." Zymergen, Machine learning, automation, and biotech, Strata + Hadoop World, Make Data Work conference, Presentation, London, UK, May 5, 2015, 49 pages http://cdn.oreillystatic.com/en/assets/1/event/132/The%20datadriven%20future%20of%20biotechnology%20Presentation.pdf.
Wilson et al., "Genotype specification language." ACS Synthetic Biology (2016); 5.6: 471-478.
Alper et al, Construction of lycopene-overproducing *E. coli* strains by combining systematic and combinatorial gene knockout targets, Nature Biotechnology May 20015, vol. 23, No. 5, pp. 612-616.
Buchholz et al, Platform Engineering of Corynebacterium glutamicum with Reduced Pyruvate Dehydrogenase Complex Activity for Improved Production of L-Lysine, L-Valine, and 2-Ketoisovalerate, Applied and Environmental Microbiology, Sep. 2013, vol. 79, No. 18, pp. 5556-5575.
Gardner et al, Production of Citric Acid by Mutants of Aspergillus niger, 1956, J. gen. Microbiol. 14, pp. 228-237.
Ikeda et al, A genome-based approach to create a minimally mutated Corynebacterium glutamicum strain for efficient L-lysine production, Society for Industrial Microbiology 2006, 6 pages.
Lee et al, A Highly Characterized Yeast Toolkit for Modular, Multipart Assembly, ACS SyntheticBiology 2015, pp. 975-986.
Lee et al, Systems biotechnology for strain improvement, Trends in biotechnology, vol. 23 No. 7, Jul. 2005, 10 pages.
Ohnishi et al, A novel methodology employing Corynebacterium glutamicum genome information to generate a new L-lysine-producing mutant, Appl Microbiol Biotechnol (2002) 58: 7 pages.
Snitkin et al, Epistatic Interaction Maps Relative to Multiple Metabolic Phenotypes, PLoS Genetics, Feb. 2011, vol. 7, Issue 2, 15 pages.
Trikka et al, Iterative carotenogenic screens identify combination of yeast gene deletions that enhance sclareol production, BioMed Central, Microbial Cell Factories 2015, 14:60, 19 pages.
Wang et al, Programming cells by multiplex genome engineering and accelerated evolution, Nature vol. 460, Aug. 13, 2009, 6 pages.
Beal et al, 2012, An End-to-End Workflow for Engineering of Biological Networks from High-Level Specifications, ACS SyntheticBiology, pp. 317-331, Supporting Information: Method Detail for "An End-to-End Workflow for Engineering of Biological Networks from High-Level Specifications" pp. 1-13.
Concise Description of the Relevance of Alper et al., filed in U.S. Appl. No. 15/396,230 on Dec. 7, 2017, 2 pgs.
Concise Description of the Relevance of Beal et al. and Platt et al., filed in U.S. Appl. No. 15/140,296 on May 18, 2018, 9 pgs.
Concise Description of the Relevance of Beal et al., filed in U.S. Appl. No. 15/140,296 on May 18, 2018, 7 pgs.
Concise Description of the Relevance of Bilitchenko et al., filed in U.S. Appl. No. 15/140,296 on May 18, 2018, 7 pgs.
Concise Description of the Relevance of Buchholz et al., filed in U.S. Appl. No. 15/396,230 on Dec. 7, 2017, 2 pgs.
Concise Description of the Relevance of Gardner et al., filed in U.S. Appl. No. 15/396,230 on Dec. 7, 2017, 1 pg.
Concise Description of the Relevance of Ikeda et al. and Trikka et al., filed in U.S. Appl. No. 15/396,230 on Dec. 7, 2017, 9 pgs.
Concise Description of the Relevance of Ohnishi et al., filed in U.S. Appl. No. 15/396,230 on Dec. 7, 2017, 1 pg.
Concise Description of the Relevance of Pedersen et al., filed in U.S. Appl. No. 15/140,296 on May 18, 2018, 7 pgs.
Concise Description of the Relevance of Platt et al., filed in U.S. Appl. No. 15/140,296 on May 18, 2018, 3 pgs.
Concise Description of the Relevance of Wang et al., filed in U.S. Appl. No. 15/396,230 on Dec. 7, 2017, 2 pgs.
Concise Description of the Relevance of Wilson et al. and Platt et al., filed in U.S. Appl. No. 15/140,296 on May 18, 2018, 10 pgs.
Concise Description of the Relevance of Wilson et al., filed in U.S. Appl. No. 15/140,296 on May 18, 2018, 6 pgs.
PCT Third Party Observation submitted Apr. 6, 2018 for international Patent Application No. PCT/US2016/065465, 12 pages.
PCT Third Party Observation submitted Aug. 24, 2018 for International Patent Application No. PCT/US2017/029725, 5 pgs.
Third Party Submission filed in U.S. Appl. No. 15/140,296 on May 1, 2018, 3 pgs.
Third Party Submission submitted Dec. 7, 2017 for U.S. Appl. No. 15/396,230, 14 pages.
Third Party Pre-Issuance Submission Transmittal, filed in U.S. Appl. No. 15/140,296 on May 18, 2018, 2 pgs.
Third Party Pre-Issuance Submission Transmittal, filed in U.S. Appl. No. 15/396,230 on Dec. 7, 2017, 2 pgs.
Third Party Submission Under 37 CFR 1.290 Concise Description of Relevance, filed in U.S. Appl. No. 15/140,296 on May 18, 2018, 5 pgs.
Third Party Submission Under 37 CFR 1.290 Concise Description of Relevance, filed in U.S. Appl. No. 15/396,230 on Dec. 7, 2017, 8 pgs.
Written Opinion for PCT/US2017/029725 dated Sep. 8, 2017, 6 pages.
International Search Report for PCT/US2017/029725 dated Sep. 8, 2017, 4 pages.
European Examination Report, Application No. 17722313.8, dated Apr. 13, 2021, 10 pages.
Indian Patent Application No. 201847044160, Examination Report dated May 28, 2021 (5 pages).
Tobler et al., "The SNPlex Genotyping System: A Flexible and Scalable Platform for SNP Genotyping," Journal of Biomolecular Techniques (Dec. 2005), vol. 16, Issue 4, pp. 398-406.
Japanese Office Action; Application No. 2018-555880; dated Jul. 5, 2021; 3 pages.
Chinese Office Action; Application No. 201780035220.X; dated Aug. 3, 2021; 7 pages.
English-language Summary of Chinese Office Action; Application No. 201780035220.X; dated Aug. 3, 2021; 11 pages.
Pedersen et al., "Towards programming languages for genetic engineering of living cells," J.R. Soc. Interface (Apr. 15, 2009), The Royal Society, 6: S437-S450 (published online).†
Bilitchenko et al., "Eugene—A domain specific language for specifying and constraining synthetic biological parts, devices, and systems," PLoS ONE (Apr. 29, 2011) 6(4):e18882 (published online).†
Wilson et al., "Genotype Specification Language," ACS Synth Biol. (Feb. 17, 2016), ACS Publications, 5(6): 471-478 (published online)†
Beal et al., "An End-to-End Workflow for Engineering of Biological Networks from High-Level Specifications." ACS Synth. Biol. (Jul. 10, 2012), ACS Publications, 1: 317-331 (published online).†

† cited by third party

MICROBIAL STRAIN DESIGN SYSTEM AND METHODS FOR IMPROVED LARGE-SCALE PRODUCTION OF ENGINEERED NUCLEOTIDE SEQUENCES

BACKGROUND

Microbe engineering enables the generation of novel chemicals, advanced materials, and pharmaceuticals. In one business model, a strain design company, on behalf of itself or third parties, may modify a previously described DNA segment to enhance the metabolic production of a microbial host by improving output properties such as yield, productivity, optimal growth temperature, growth rate, and titer. Many conventional efforts have been focused on small-batch research yields. To achieve microbe engineering at an industrial scale, however, requires storing and sharing vast amounts of DNA sequence information. Multiple teams must be able to share design ideas, scientists must be able to communicate with production engineers, and project managers must be able to track details from the early stages of conception to the final stages of evaluation.

High-throughput production of modified microbes requires high-throughput strain design. Robots are capable of building hundreds to thousands of strains at once, and design tools must be able to match this capacity. Large experiments may be imagined by exploring different combinations of the same few elements or by trying many small changes to a basic design. An ideal storage and exchange format would structure data such that these relationships are maintained and could be interpreted by other software tools in the realm of design, construction, or evaluation.

In particular, developers face the challenge of communicating design concepts at the level of DNA parts, DNA assemblies, and engineered cells lines: (1) between the strain design company and partner businesses, as well as (2) between development and operations departments within the strain design company.

Previous efforts have led to proposals for standardized descriptions of DNA parts. For example, Synthetic Biology Open Language Visual (SBOL Visual) is an open-source graphical notation that uses schematic "glyphs" to specify genetic parts, devices, modules, and systems. See also *BBF RFC 108: Synthetic Biology Open Language (SBOL) Version 2.0.0*, editors Bartley, et al., Jul. 31, 2015, which is incorporated by reference herein in its entirety.

The SBOL standard's foundation is a "core data model" for the specification of DNA-level designs. This SBOL core defines biological building blocks as DNA components and enables their hierarchical composition, allowing specification of the substructure and construction of each design component. The DNA component is an entity describing a region of DNA. The fundamental information is the underlying DNA sequence. Decorating that sequence are sequence annotations (metadata). A sequence annotation describes a region of nucleotides in that sequence, such as a promoter, and an orientation. Each sequence annotation can also be represented as a DNA component.

The SBOL core also offers a "collection" data structure to group DNA components into libraries and catalogs. See, e.g., Bartley, et al., *BBF RFC 108: Synthetic Biology Open Language (SBOL) Version 2.0.0*, at Sections 5.2, 6, 7.10.

SBOL provides a set of visual symbols and a data format that correspond to the structure and function of gene sequences. Its goal is to provide a standardized format for communication of novel synthetic designs. SBOL, however, is not itself a programming model for executing specific changes to a given genome or gene sequence. Although SBOL describes the structure of DNA segments and the functional behavior of component parts, it does not provide a compact notation for describing operations to be performed on DNA sequences. Operations must be defined via annotations on the DNA sequence itself, or through extension data model elements within the XML language of SBOL. In either case, these annotations or extension data model elements will be proprietary to each organization or user who defines and inserts them, rendering them as non-standard extensions in any case. These annotations or data structures are placed on the final DNA output sequence, which demarcate the inputs that give rise to that sequence. Because of this structure, the logical or physical order of operations associated with the production of the sequence is not inherently captured in the structure of the data itself.

Furthermore, SBOL, like Genbank and other file formats for communicating explicit DNA sequences, requires that the user provide a separate SBOL description of each DNA sequence to be created or proposed. For example, 1,000 genome edits would be described by enumerating 1,000 variant DNA sequences; a collection of edits cannot be described in terms of the underlying parts and various combinations thereof. This format is cumbersome for users to edit directly without specialized tools and is inefficient in storage space compared to other serialization formats (e.g., a binary format such as Avro).

The j5 software package offered by TeselaGen Biotechnology is an example of many DNA editing packages that provide, among other features, automated methods for defining what DNA parts are required to build DNA constructs. Typically, these tools take as input a table of information where each row represents one construct to be built and each column contains the pieces that should go into building it. The tool then outputs lists of DNA sequences with information about how those sequences should be used in a common laboratory protocol.

The j5 system relies on a number of CSV (spreadsheet) files to construct its outputs. In these spreadsheets, each row corresponds to a DNA part (named sequence) or other output. Unlike SBOL, GHS or other systems, j5 does permit concise combinatorial assembly by referencing "combinatorial bins" in its target part order list file. j5, however, requires that the scientist have specific knowledge of the assembly method to use, and to encode and arrange the parts in a manner particular to the assembly method (LHR, Gibson, etc). j5 does not permit a decoupling of logical (syntactic) changes to the DNA from the physical means of accomplishing those changes.

Furthermore, j5 is limited by its rigid spreadsheet-based input format. j5 "scripts" are collections of spreadsheets that specify lists of items to concatenate together. It is required that a user specify a complete assembly as a series of individual parts. j5 does not permit arbitrarily flexible edits (such as changing an individual base pair) by way of modifying existing DNA sequences in arbitrary fashion (insertions, deletions, replacement, etc.).

Finally, j5 requires that a constant set of parameters for an assembly technique be used. A single "parameters file" spreadsheet provides global parameters (melting temperature, PCR product size, etc.) for reactions to accomplish the entire assembly. j5 does not contemplate the application of parameters or different assembly techniques to intermediate sub-assemblies of the overall assembly process.

GSL is a proprietary language developed by Amyris, Inc. for the purpose of specifying collections of edits that give rise to new strain definitions. GSL allows users to define edits using a language offering both high- and low-level sequence editing operators. In each case, the user must explicitly write out combinations of subsequences to be combined. GSL does not provide list or looping constructs to allow users to write scripts that combine input arguments or DNA elements in combinatorial fashion; the script itself is O(n) in terms of the number of output sequences desired. Furthermore, GSL expects that edits will be performed using a specific collection of editing techniques that work on editing sites associated with particular host organisms used by Amyris, predominantly centered on concatenating elements to be inserted at a known site in the host DNA sequence. GSL is not extensible to a variety of DNA modification patterns the user may wish to perform in the future, across strains, plasmids, or arbitrary DNA sequences or subsequences independent of host.

The Eugene language permits combinatorial DNA design through the use of its permute( ) function. See L. Bilitchenko et al., Eugene—A Domain Specific Language for Specifying and Constraining Synthetic Biological Parts, Devices, and Systems, PLoS ONE, Vol. 6, Issue 4, Apr. 29, 2011. This allows more concise scripts that are O(n) in size in terms of the number of input parts and combinators, rather than in the number of outputs. Thus, it permits generation of many more sequences than GSL or other systems (e.g., SBOL). Eugene offers users the Rule predicate which allows filtering on various properties. Furthermore, multiple Devices can be concatenated together using alignment on features (annotations) of the DNA or in various orders based on other properties. The Rule syntax uses a logical programming structure to define various constraints that, collectively, bind Devices together in orders that only satisfy all of the rules, using a constraint-satisfaction language in the same vein as proof languages like PROLOG. The number of rules and the specific syntax used to define them is cumbersome for scientific users who lack software engineering experience. The predicate logic syntax in particular requires that users who may have only a passing familiarity with imperative languages such as Perl or Python (as can be expected of many microbiologists) think and enter input in a programming style that is very foreign without previous formal training in computer science.

Eugene essentially provides as an input to a gene manufacturing process a nucleotide sequence to be manufactured. From that information, the assembler of the genome is left to determine the best nucleotide parts and workflow to manufacture the sequenceIn large-scale operations, many thousands of sequences may be generated by genomic design program like Eugene. For example, the program may generate 10,000 modified genomes, which would occupy on the order of 50-100 GB of storage space. This information would not fit in a typical memory at this time, and would instead require, for example, slower disk-based access. Embodiments may employ, e.g., SBOL to represent the output DNA components. Current commercial computer systems cannot load and operate efficiently on a 50-100 GB SBOL file. Such operations may crash or cause unacceptable delays in processing. Thus, it is desired to develop means to overcome the challenges rooted in computer technology when implementing large-scale sequence designs in computer systems.

SUMMARY

Embodiments of the invention provide processes, systems, and data structures for simultaneously introducing multiple mutations in multiple parent nucleotide sequences to transform them into a large set of mutated sequences. Embodiments of the invention improve industrial-scale genomic design and manufacture by, e.g., reducing time and complexity for the design and building of nucleotide sequences.

The application of data science to genomic design and manufacturing has, however, given rise to challenges such as those described above in the background section. In particular, high-throughput nucleotide sequence design can lead to the generation of an unmanageable number of output sequences that create too much data for simple computer memory, requiring the use of more complex memory management systems, incorporating, for example, disk-based storage. Moreover, processing a large number of such output sequences can lead to unacceptably slow processing times or even processing failure. Embodiments of the invention overcome these technical obstacles, in part by providing the capability to generate a manageable amount of sequence data that avoids the need for complex memory management schemes and unacceptably slow processing of sequence data during design and manufacture.

Embodiments of the invention also provide recursive data structures that inform the gene manufacturing process of beginning and intermediate nucleotide parts, other nucleotide sequence synthesis inputs (e.g., primers, enzymes, reagents), and environmental factors (e.g., temperature). The data structure may also specify the workflows of beginning and intermediate steps in a desired gene manufacturing process. The consideration of this information better informs the manufacturing process, thereby enabling optimization of manufacture over a number of conditions (e.g., price and availability of parts and promoters, efficiency of workflow selection), i.e., leading to improvements in yield, scalability, processing time and other factors in order to overcome the challenges posed by the large-scale computer-aided design and manufacture of genomes in microbial strains and other host cells.

Using some or all of the features of the embodiments herein, scientists can define very large sets of nucleotide sequences (e.g., orders of magnitude of a million or more) in a compact programming format, while, counterintuitively, also efficiently controlling low-level, finely granular details of the assembly process. Part of this control provides for the generation of more manageable subsets of sequences to avoid burdens that would otherwise be placed on storage and processing capabilities in genomic design and manufacturing systems.

In particular, embodiments of the invention include the generation of a factory order to control production of nucleotide sequences by a gene manufacturing system. Systems, methods, and computer readable media are described herein that: receive an expression indicating an operation on sequence operands, each representing at least one nucleotide sequence part; evaluating the expression to a sequence specification, wherein the sequence specification comprises a data structure including one or more first-level operations and one or more second-level operations; and generating a factory order based upon execution of the one or more first-level operations and the one or more second-level operations. In a recursive manner, the one or more first-level operations operate on at least one first-level sequence operand, the value of which is resolved by execution of one or more of the second-level operations. The factory order may then be provided to the gene manufacturing system to assemble the sequence parts into nucleotide sequences represented by the sequence specification.

In embodiments of the invention, the factory order may be based on parameters, included in the specification data structure, that relate to how one or more of the first-level operations or one or more second-level operations are to be reified (physically achieved) by the gene manufacturing system. In some embodiments, the parameters may include a first parameter to be used by the gene manufacturing system in the reification of a first second-level operation of the one or more second-level operations, and a second parameter, different from the first parameter and representing the same category of parameters as the first parameter, to be used by the gene manufacturing system in the reification of a second second-level operation of the one or more second-level operations. As examples, the first parameter may indicate a first assembly method, temperature, sequence part source, or primer source, and the second parameter may indicate a second, different assembly method, temperature, sequence part source, or primer source, respectively.

In embodiments of the invention, sampling may be employed to reduce the need for large storage capacity and heavy processing power by selecting for execution only a subset of sequence specifications, e.g., "child" sequence specifications at an intermediate or low level in the recursive data structure that act as inputs/operands for sequence specifications one level higher in the data structure. (Note that the "first-level operations" in the sequence specification referred to above and elsewhere herein may not necessarily reside at the top-level of the data structure hierarchy, but may instead reside in a child sequence specification below the top-level.) The selection of the subset of sequence specifications for execution may be based upon, for example, random sampling, selecting only the first K or last K specifications, or weighting the specifications. The weighting may be based upon the phenotypic properties of nucleotide sequences assembled as a result of prior factory orders. Sequences assembled during a prior factory run may be observed to exhibit a high degree of a desired phenotypic property. Those sequences may have been generated from child sequence specifications that specified, for example, particular promoters. This information may be used to favorably weight the child specifications specifying those promoters to increase the chance they will be executed and incorporated in the current factory order.

In embodiments of the invention, the recursive data structure may be used to specify useful operations like replacement of promoters associated with genes in a promoter-gene-terminator sequence. For example, a first-level function may be a replace function having an operand that is resolved by execution of a second-level location-resolution function that locates the promoters in a sequence. In particular in this example, evaluating a replace/location-resolution expression comprises creating a sequence specification that represents replacing replaceable promoter regions of a sequence including multiple promoter-gene-terminator sequences represented by a first sequence operand with replacement promoters represented by a second sequence operand. Execution of the first sequence operand identifies the replaceable regions.

These and other embodiments are more fully described below.

DETAILED DESCRIPTION

The present description is made with reference to the accompanying drawings, in which various example embodiments are shown. However, many different example embodiments may be used, and thus the description should not be construed as limited to the example embodiments set forth herein. Rather, these example embodiments are provided so that this disclosure will be thorough and complete. Various modifications to the exemplary embodiments will be readily apparent to those skilled in the art, and the generic principles defined herein may be applied to other embodiments and applications without departing from the spirit and scope of the disclosure. Thus, the present disclosure is not intended to be limited to the embodiments shown, but is to be accorded the widest scope consistent with the principles and features disclosed herein.

System Overview

Figure 1:
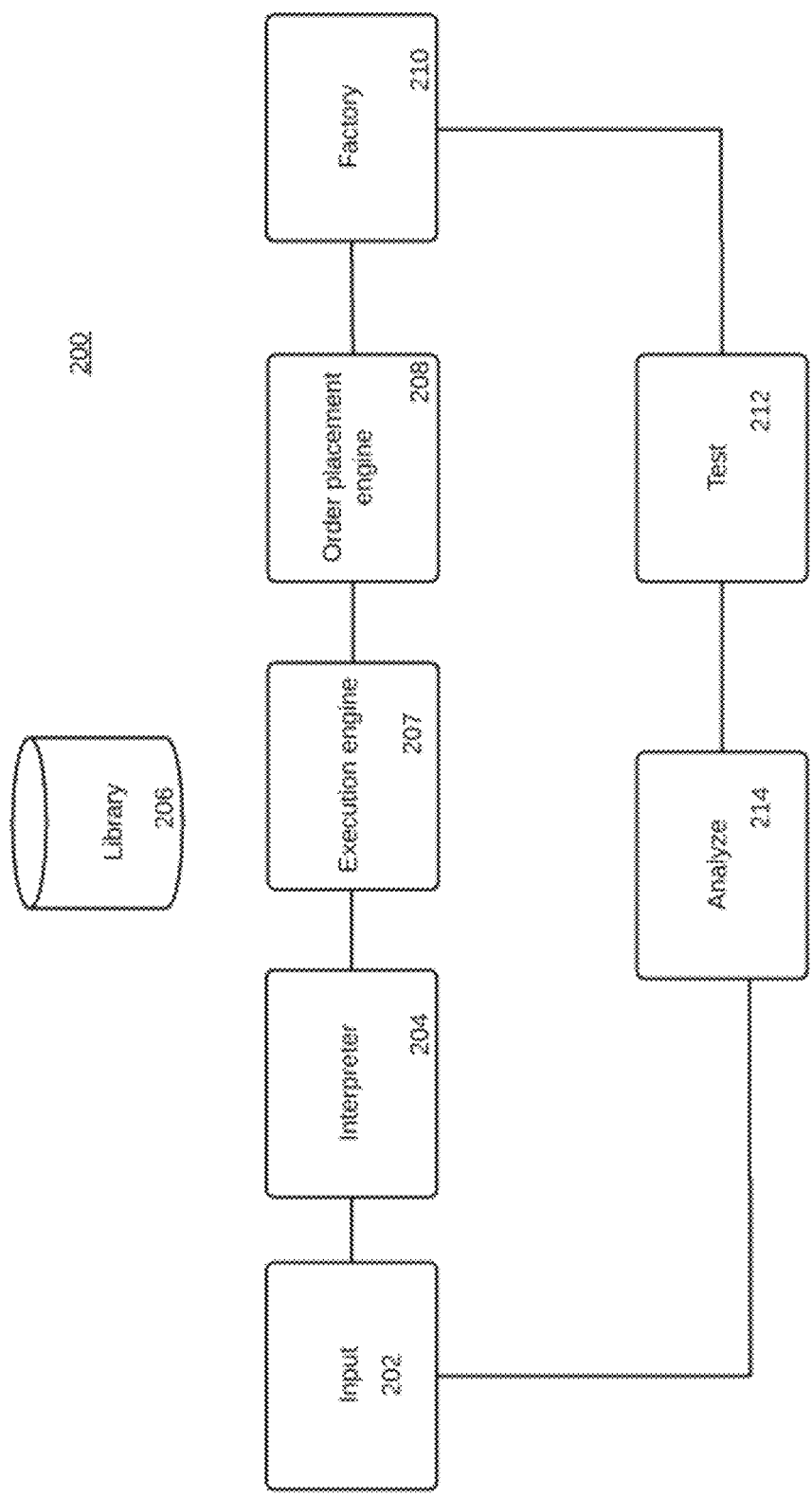
FIG. 1 illustrates a laboratory information management system of embodiments of the invention for the design, building, testing, and analysis of nucleotide sequences.
Figure 2:
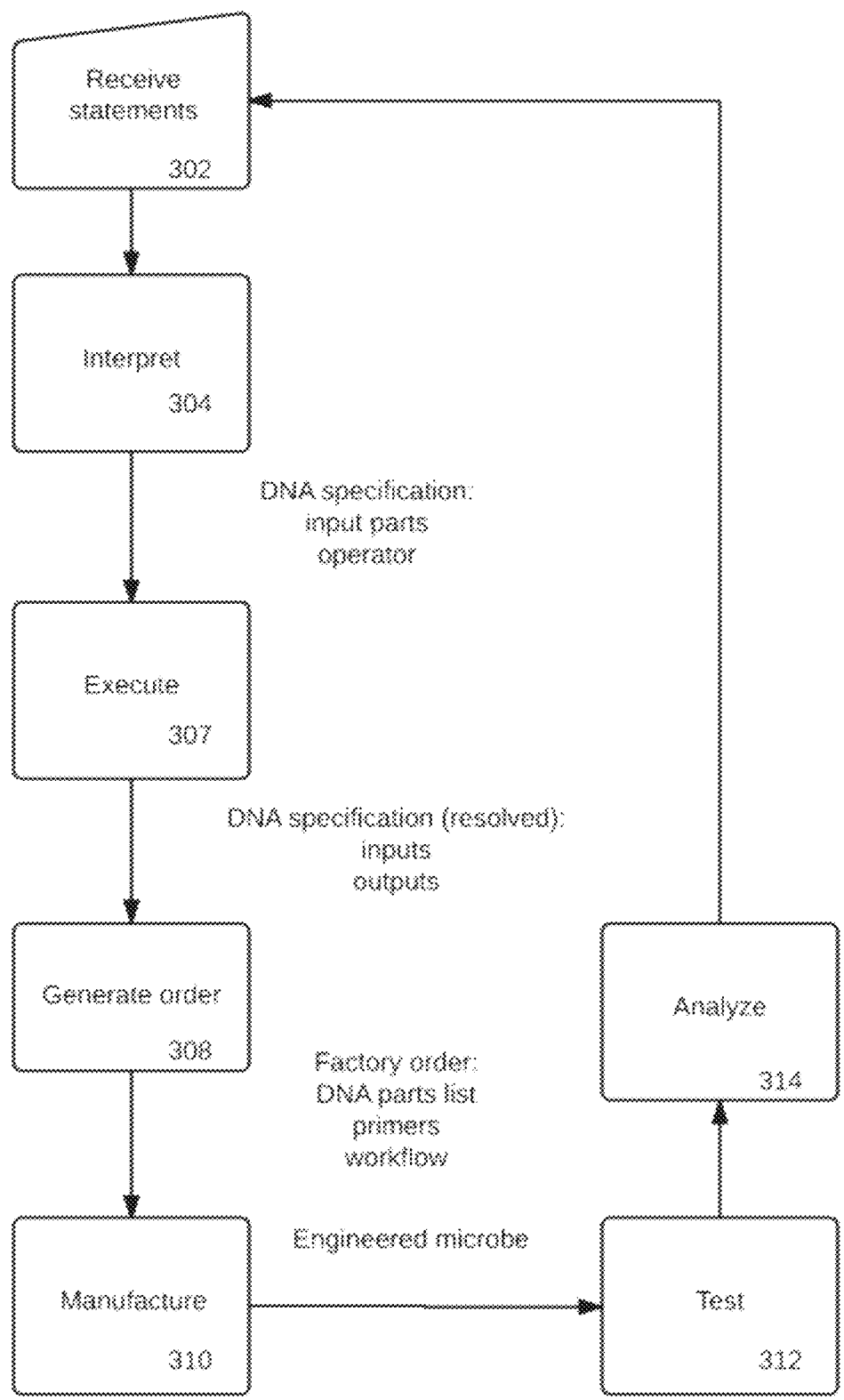
FIG. 2 is a flow chart illustrating a process for designing and building nucleotide sequences, according to embodiments of the invention.

FIG. 1 is a system diagram of a laboratory information management system (LIMS) 200 of embodiments of the invention for the design, building, testing, and analysis of DNA sequences. FIG. 2 is a corresponding flow diagram. In embodiments of LIMS, one or more changes are made to an input DNA sequence at a time, resulting in a single output sequence for each change or change set. To optimize strains (e.g., manufacture microbes that efficiently produce an organic compound with high yield), LIMS produces many such DNA output sequences at a time, so that they may be analyzed within the same timeframe to determine which host cells, and thus which modifications to the input sequence, best achieve the desired properties. As will be seen below, the genomic design language of embodiments of the invention provides compact, human-readable expressions to generate many genome designs in parallel.

In some embodiments the system enables the design of multiple nucleotide sequence constructs (such as DNA constructs like promoters, codons, or genes), each with one or more changes, and creates a work order (generally referred to herein as a "factory order") to instruct a gene manufacturing system or factory 210 to build the nucleotide sequence constructs in the form of microbes carrying the constructs. Such microbes include, without limitation, hosts such as bacteria, fungi, and yeast. According to the system, the microbes are then tested for their properties (e.g., yield, titer). In feedback-loop fashion, the results are analyzed to iteratively improve upon the designs of prior generations to achieve more optimal microbe performance.

Although the disclosure primarily refers to DNA constructs, those skilled in the art will recognize that the embodiments herein may readily be extended to any nucleotide sequence/nucleic acid sequence (e.g., messenger RNA, any such sequence in an IUPAC alphabet) and is not just limited to DNA sequences. Moreover, although the design, build, test and analysis process is described herein primarily in the context of microbial genome modification, those skilled in the art will recognize that this process may be used for desired gene modification and expression goals in any type of host cell.

Referring to FIGS. 1 and 2 in more detail, an input interface 202, such as a computer running a program editor, receives statements of a program/script that is used to develop the design of one or more DNA output sequences (see 302 in FIG. 2). Such a genomic design program language may be referred to herein as the "Codon" programming language developed by the assignee of the present invention. A powerful feature of embodiments of the invention is the ability to develop designs for a very large number of DNA sequences (e.g., microbial strains, plasmids) within the same program with just a few procedural statements.

Program statements may comprise a keyword, specifying an operation, and at least one argument, a function call designated by a function name to call followed by zero or more arguments (whose return value is then discarded upon evaluation), or an assignment of an expression or value to a variable which can be included in subsequent expressions by the variable's name. An expression is a collection of symbols that can be evaluated (resolved) to a value. A function call may be used as a statement or an expression.

Figure 7:
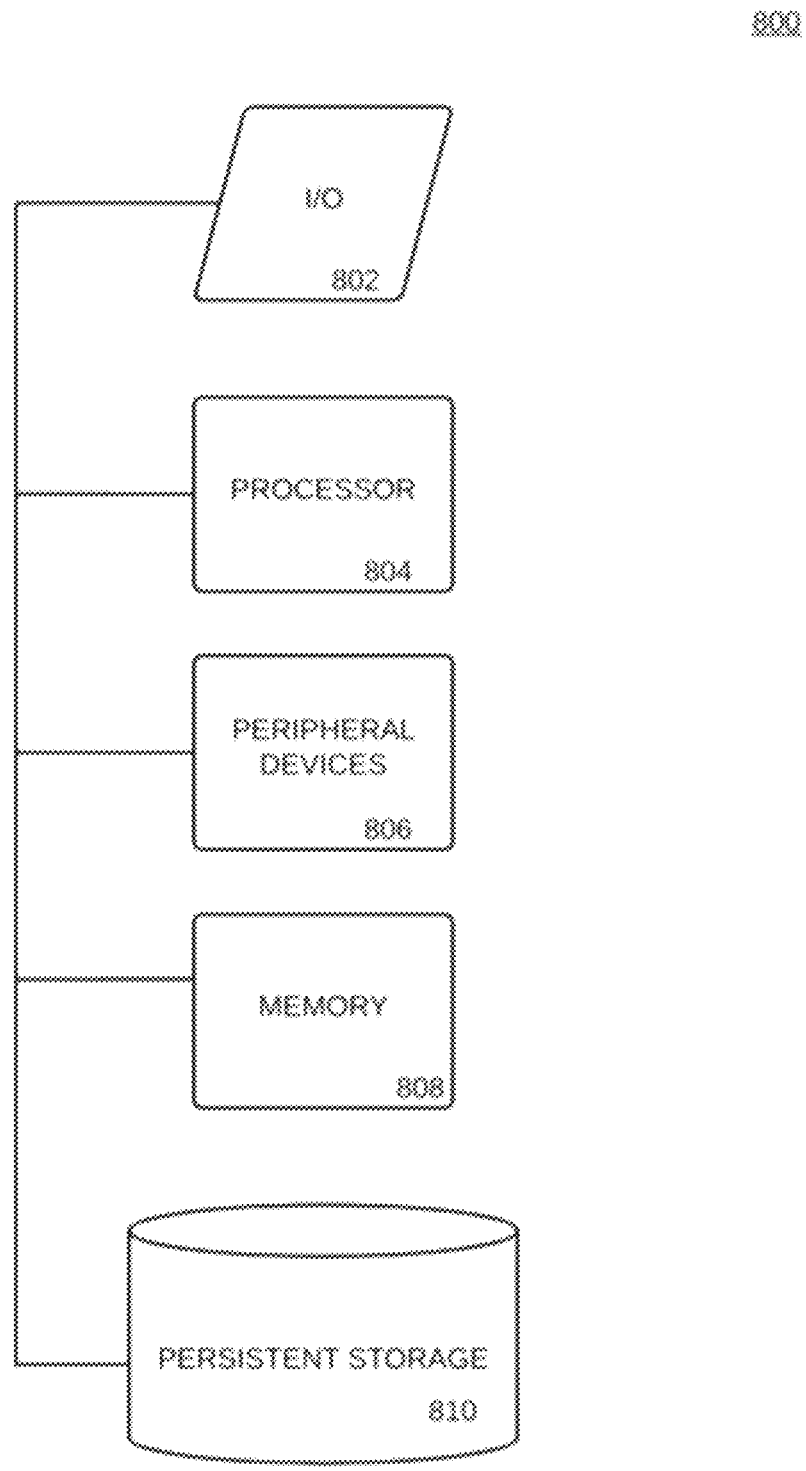
FIG. 7 illustrates an example of a computer system that may be used to implement embodiments of the invention.

Here, the editor enables a user to enter and edit the program, e.g., through graphical or text entry or via menus or forms using a keyboard and mouse on a computing device, such as that describe with respect to FIG. 7. Those skilled in the art will recognize that other input interfaces 202 may be employed without the need for direct user input, e.g., the input interface 202 may employ an application programming interface (API), and receive statements in files comprising the program from another computing device. The input interface 202 may communicate with other elements of the system over local or remote connections.

An interpreter or compiler/execution unit 204 evaluates program statements into novel DNA specification data structures of embodiments of the invention (304). Data structure details will be described below. (A "DNA specification" may also be referred to herein according to its data type "DnaSpecification." Moreover, the term "DNA specification" is not limited to just DNA sequences, but rather applies to any nucleotide sequence. The "DNA specification" as used herein refers to a specification of how to create one or more DNA/nucleotide sequence(s) from input arguments and an instruction such as "concatenate." If the DNA specification is evaluated, then it may also record its output sequences as described below.)

The terms "interpreter" and "compiler/execution unit" shall be used interchangeably herein, as the invention may be implemented with either an interpreter or a compiler; the program statements may be either interpreted or compiled. If a compiler is employed, it would be followed by an execution unit in the system of the invention.

Typically, at the end, the program script will include a "create" statement identifying the DnaSpecification representing the program's final output to include in a "design campaign." The design campaign itself is a precursor to a factory order for the production of DNA sequences, as will be described below. One or more create statements may be provided; if multiple such statements are used, the collection of DNA specifications is held together in a top-level "list" specification.

The interpreter 204 evaluates the DNA specification argument of the create statement into the design campaign represented via the DnaSpecification data type. The create statement itself may include an indicator (e.g., a flag or other indicator) read by an order placement engine 208 indicating that the argument of the create statement is to be used to generate a factory order for producing a sequence identified by the argument.

In embodiments of the invention, at this stage, the interpreter 204 may execute the operations specified by the DNA specification so that its data structure includes resolved outputs. However, in other embodiments, the interpreter 204 would not execute those operations, and the output DNA specification data structure would not include any outputs that have been resolved. Instead, as described below, an execution engine 207 would resolve the outputs.

In evaluating expressions, the interpreter 204 may refer to one or more sources of DNA sequence data, such as custom/local databases, public databases, or user-provided files (collectively referred to herein as a "library" for the sake of convenience). Similar to the design of electronic circuits, synthetic biology designs may be composed hierarchically from libraries of reusable components. A library 206 may include data (e.g., annotations) reflecting properties of DNA sequences and microbes. For example, the library may include data representing the DNA sequences for different strains of *E. coli*, the locations of promoters and terminators within known DNA sequences, and the locations of genes within a microbial strain. The library may, for example, include a database containing thousands of DNA components—some of them entire microbial strain genomes, some of them smaller gene parts. Codon statements may refer to any of these by a unique ID. The library 206 may also refer to the outputs of prior Codon evaluation runs—design campaigns or factory orders—both of which may be embodied in the DnaSpecification data type. In particular, the library 206 may store "libraries" of genotype-phenotype correlation data resulting from the analysis phase describe herein, to allow for the selection of base strains and genetic modifications as candidates to achieve desired phenotypic properties for new factory runs.

DnaSpecifications may also be referred to by ID. According to embodiments of the invention, IDs may be issued by the interpreter 204 in non-overlapping sequences to DnaComponents and DnaSpecifications alike, so they may be used interchangeably as inputs within a library. However, by using separate lookup functions for DnaComponents and DnaSpecifications, the system and the user can differentiate between DnaComponents and DnaSpecifications even if the same ID would be a valid identifier for either a DnaComponent or DnaSpecification within the collection of each type. In addition, the library may store a DNA sequence in a file (typically in FASTA or genbank format) that can be used in the Codon script.

In embodiments, an execution engine 207, instead of the interpreter 204, may execute the DNA specification (307). For example, the execution engine 207 may execute one or more operators specified by the DNA specification, applying the operators to the appropriate inputs specified by the DNA specification. At this point, the DNA specification data structure would include the resulting resolved outputs, as well as the one or more operators and inputs (and parameters, discussed below). These outputs may be expressed as an ordered list of DNA components (e.g., cross-product elements described in examples below).

In embodiments, the order placement engine (alternatively called a specification/campaign interpreter or factory order placer) 208 interprets the DNA specification representing the design campaign and determines which intermediate DNA parts will be produced or will be needed as inputs to the factory 210 (308). In general, in some embodiments, the factory order placer 208 requires two inputs: a DnaSpecification and workflow information to indicate what is being built (DnaSpec) and how the user intends to build it (workflow). Based on that, the factory order placer 208 can compute the intermediate parts that will be required for that workflow process using known algorithms that obey known heuristics and other properties (e.g., optimal melting temperature to run on common equipment). In embodiments of the invention, the sequence specification itself may specify intermediate inputs as well as parameters indicating workflows and properties for beginning, intermediate and final operations.

The resulting factory order may include a combination of a prescribed set of steps, as well as the parameters, inputs and outputs for each of those steps for each DNA sequence to be constructed. The factory order may include a DNA parts list including a starting microbial base strain, a list of primers, guide RNA sequences, or other template components or reagent specifications necessary to effect the workflow, along with one or more manufacturing workflow specifications for different operations within the DNA specification, as discussed further below. The order placement engine 208 may refer to the library 206 for this information. This information is used to reify the design campaign operations in physical (as opposed to in silico) form at the factory 210 based upon conventional techniques for nucleotide sequence synthesis, as well as custom techniques developed by users or others.

For example, assume a recursive DNA specification has a top-level function of circularize and its input is a chain of concatenate specifications. The factory order placer 208 may interpret that series of inputs such that a person or robot in the lab may perform a PCR reaction to amplify each of the inputs and then assemble them into a circular plasmid, according to conventional techniques or custom/improved techniques developed by the user. The factory order may specify the PCR products that should be created in order to do the assembly. The factory order may also provide the primers that should be purchased in order to perform the PCR.

In another example, assume a DNA specification specifies a top-level function of replace. The factory order placer 208 may interpret this as a cell transformation (a process that replaces one section of a genome with another in a live cell). Furthermore, the inputs to the replace function may include parameters that indicate the source of the DNA (e.g. cut out of another plasmid, amplified off some other strain).

The order placement engine 208 may communicate the factory order to the factory 210 over local or remote connections. Based upon the factory order, the factory 210 may acquire short DNA parts from outside vendors and internal storage, and employ techniques known in the art, such as the Gibson assembly protocol or the Golden Gate Assembly protocol, to assemble DNA sequences corresponding to the input designs (310). The factory order itself may specify which techniques to employ during beginning, intermediate and final stages of manufacture. For example, many laboratory protocols include a PCR amplification step that requires a template sequence and two primer sequences. The factory 210 may be implemented partially or wholly using robotic automation.

According to embodiments of the invention, the factory order may specify the production in the factory 210 of hundreds or thousands of DNA constructs, each with a different genetic makeup. The DNA constructs are typically circularized to form plasmids for insertion into the base strain. In the factory 210, the base strain is prepared to receive the assembled plasmid, which is then inserted.

The resulting DNA sequences assembled at the factory 210 are tested using test equipment 212 (312). During testing, the microbe strains are subjected to quality control (QC) assessments based upon size and sequencing methods. The resulting, modified strains that pass QC may then be transferred from liquid or colony cultures on to plates. Under environmental conditions that model production conditions, the strains are grown and then assayed to test performance (e.g., desired product concentration). The same test process may be performed in flasks or tanks.

In feedback-loop fashion, the results may be analyzed by analysis equipment 214 to determine which microbes exhibit desired phenotypic properties (314). During the analysis phase, the modified strain cultures are evaluated to determine their performance, i.e., their expression of desired phenotypic properties, including the ability to be produced at industrial scale. The analysis phase uses, among other things, image data of plates to measure microbial colony growth as an indicator of colony health. The analysis equipment 214 is used to correlate genetic changes with phenotypic performance, and save the resulting genotype-phenotype correlation data in libraries, which may be stored in library 206, to inform future microbial production.

LIMS iterates the design/build/test/analyze cycle based on the correlations developed from previous factory runs. During a subsequent cycle, the analysis equipment 214, alone or in conjunction with human operators, may select the best candidates as base strains for input back into input interface 202, using the correlation data to fine tune genetic modifications to achieve better phenotypic performance with finer granularity. In this manner, the laboratory information management system of embodiments of the invention implements a quality improvement feedback loop.

Data Structures

Unlike some conventional techniques for nucleotide sequence assembly, embodiments of the invention do not require an input of literal strings directly representing desired sequences. The editor or other input interface may instead, or in addition, receive statements expressed in a high-order genomic description language of embodiments of the invention. As indicated above, each high-order statement evaluates to a "DNA specification," having data type DnaSpecification, in embodiments of the invention. The DNA specification is a data structure indicating at least one operation on at least one DNA part represented by at least one DNA operand (of data type DnaInput). (A DNA "part" herein refers to a DNA sequence, e.g., a promoter, a gene, a terminator, or any combination thereof. More generally, the invention applies to any nucleotide sequence parts.) A DnaInput may be either a DnaComponent (an unambiguous representation of a single DNA sequence) or another DnaSpecification. The input itself may be the output of a previous Codon statement within the script or a Codon script output from a prior run/evaluation of the script, giving rise to a recursive data structure describing an ordered set of operations to perform on other DnaInputs specified as arguments to that DnaSpecification.

In some embodiments, a DNA specification may indicate a unary operation to be performed on a DNA part (e.g., circularize), or a binary operation to be performed on two or more DNA parts (e.g., concatenate, replace). In some embodiments, the DNA specification describes combinatorial assemblies of DNA sequences.

In short, a DNA specification may provide:
a structured collection of DNA components
a compact representation of DNA sequence relationships
a concise description of combinatorial design
a nested organization for varying layers of detail and abstraction
an exchange format between designers and manufacturers of DNA assemblies A DNA specification, in some embodiments, has three parts:
One or more sets of ordered inputs
one or more modifying actions
one set of ordered outputs Note that even in the case of functions taking "unary" inputs, such as the circularize function, the "unary" input may itself be a list of inputs. In this case, execution of the function would emit a list of circularized DNA sequences, each created from a single linear input sequence from the list. Binary functions (e.g., concatenate) may operate on two such lists, combining elements of each list as specified by a function modifier (DOT (dot product) or CROSS (cross product)) that indicates whether the elements of the two lists are combined via a "zipper" (dot product) operation (for input lists L and R, for all T, L[i] OP R[i], where "OP" represents a dot product operation), or via a "cross product" operation (for input lists L and R, for all T, for all 'j', L[i] OP R[j], where "OP" here represents a cross product operation). The result for each list may respectively be viewed as a vector or a matrix.

In some embodiments, a DNA operand within a DNA specification may be represented as either a DNA specification itself or as a DNA component, and a DNA component may represent a DNA part with a literal alphanumeric string directly representing a sequence of nucleotides. In some embodiments, as mentioned above the DNA component may also include metadata annotations describing properties of a DNA part, such as identification number, source, molecular form (e.g., linear, circular).

Notably, as described above, in some embodiments the DNA operand of the DNA specification may represent a list of DNA parts. These lists of parts can be a list of DNA components, a DNA specification, or a list of DNA specifications.

DNA Component

As a prelude to a discussion of DNA specifications, an example of a DNA component, using the dna( ) function, follows:
sequence="GATACA"
print "The sequence is:"+sequence
myFirstDna=dna(sequence)
print "Here is a DnaComponent:"
print myFirstDna
In this example, the interpreter would return:
The sequence is: GATACA
Here is a DnaComponent:
DnaComponent:
  Id: −1
  Name: dna string
  Description: literal: GATACA
  Molecular form: LINEAR
  Sequence: GATACA Using DNA components, the interpreter 204 enables specifying a DNA sequence directly in the script, or by loading it from the library. For example, a user can directly specify a short DNA sequence within the dna( ) function itself, e.g.,
myPrimer=dna("AAGTGTGAC").

Alternatively, the user may load from the library a DNA component by its ID or its name, using the dnaComponent( ) function:

```
plasmidBackbone = dnaComponent(13000109030) # Backbone referenced
by a universal ID.
anotherBackbone = dnaComponent("my-backbone") # Another backbone,
referenced by name.
```

As another alternative, a user may load from the library the DNA component that represents the sequence for a microbial strain, using the dnaForStrain( ) function:

```
aFamousSequence = dnaForStrain(7000000000) # Also accepts the strain
name as an argument.
```

More generally, a DNA sequence may be identified explicitly (i.e., from a string), from a local source (file, database), or from a public source (e.g., NCBI).

DNA Specification

With reference to the DNA specification, the interpreter 204 also enables a user to identify DNA specifications, including, for example, by loading from the library an entire DNA specification, using the dnaSpecification( ) function:

```
somePrimers = dnaSpecification(18000000000) # The argument represents
an identifier of the DNA specification.
```

This last example returns a DNA specification, whereas the previous examples returned a DNA component. Since both of these represent data of type DnaInput (the "supertype" of these two types), they are frequently interchangeable in DNA-modifying functions. That is, a program may create more complicated DNA specifications for campaigns by referencing either DNA components or DNA specifications as arguments. As will be discussed herein, even for complicated specifications, the DNA specification nevertheless provides a compact, human-readable data structure that enables the handling and creation of large numbers of sequences.

Note that the DnaInput value may be a DnaComp (DNA component; "DnaComp" and "DnaComponent" are used interchangeably herein to refer to variables or values of type "DnaComponent"), a DnaSpec (DNA specification; "DnaSpec" and "DnaSpecification" are used interchangeably herein to refer to variables or values of type "DnaSpecification"), a LocatedDnaSpec, a List[DnaComp] (a list of DNA components), or a List[DnaSpec] (a list of DNA specifications).)

Concatenation Function

The genomic design programming language and operations of embodiments of the inventions support many different functions. As an example, Codon enables concatenation of DNA parts to make larger assemblies. Codon enables specification of individual sequences with DNA component functions such as dna( ), dnaForStrain( ) and dnaComponent( ). As an example when working with individual (scalar) values, Codon enables the concatenation of two scalar strings (using the "+" concatenation function) as follows:

```
left = "left side"
right = "right side"
combinedString = left + right
```

LIMS, however, is particularly designed to design, build, test and analyze multiple DNA sequences at a time. Thus, Codon enables the user to work with lists of DNA sequences by, for example, loading a DNA specification (DnaSpec) that represents multiple DNA sequences with the function dnaSpecification( ). A program may create a DNA specification (DnaSpec) that represents a list of sequences by, for example, uploading to the library a file in known Genbank or CSV formats.

Concatenation of lists of sequences may be performed in at least two ways. If the lists are the same length, the DNA specification may specify concatenation of the items element-wise. Execution of the DNA specification by the interpreter 204 (or in other embodiments, the execution engine 207) would concatenate [a, b, c] and [d, e, f] as ad, be, cf. This function is denoted a "dot product." Alternatively, the DNA specification may specify concatenation of lists of any lengths via their Cartesian cross-product product to concatenate all possible pairs. Using the same example lists, the interpreter 204 (or in other embodiments, the execution engine 207) would concatenate the cross-product outputs as ad, ae, af, bd, be, bf, cd, ce, and cf. These outputs may be expressed as DNA components. As described herein, if the cross product would result in a very large number of outputs relative to memory capacity, the system 200 may employ sampling to reduce the number of outputs produced. As described further below, different sampling techniques may be employed, including weighting sample sets to include gene parts that have been determined during prior build and test cycles to have produced or influenced beneficial phenotypic properties. The order placement engine 208, then creates a factory order based on the outputs.

Codon represents the concatenation function in different ways. The concat( ) function will take two DnaInput arguments and concatenate the elements. The function includes a function modifier [*] or [x] between the function name and the argument list to indicate whether it is dot or cross product, as in the example below:

```
left = dnaSpecification(18000000001)
right = dnaSpecification(18000000002)
dotProducts = concat[*](left, right)
crossProducts = concat[x](left, right)
```

Because DNA concatenation is so similar to string concatenation, something that is typically done using math-like binary operators in modern programming languages, Codon offers a shorthand for concatenation: using the * or x directly to indicate concatenation, as shown in the following example.

```
left = dnaSpecification(18000000001)
right = dnaSpecification(18000000002)
dotProducts = left * right
crossProducts = left x right
moreDna = dnaSpecification(18000000003)
```

```
# You can use ( ) together with * or x to indicate associativity, which
  may affect build order.
bigCrossProduct1 = left x (right x moreDna)
bigCrossProduct2 = (left x right) x moreDna
# You can also make associativity explicit with multiple statements. Note
  that default operators of equal precedence will be evaluated left-to-right.
  (e.g., bigCrossProduct2 expresses the default.)
# The following is equivalent to bigCrossProduct1:
compoundRightSide = right x moreDna
bigCrossProduct3 = left x compoundRightSide
```

Recursion

Figure 3:
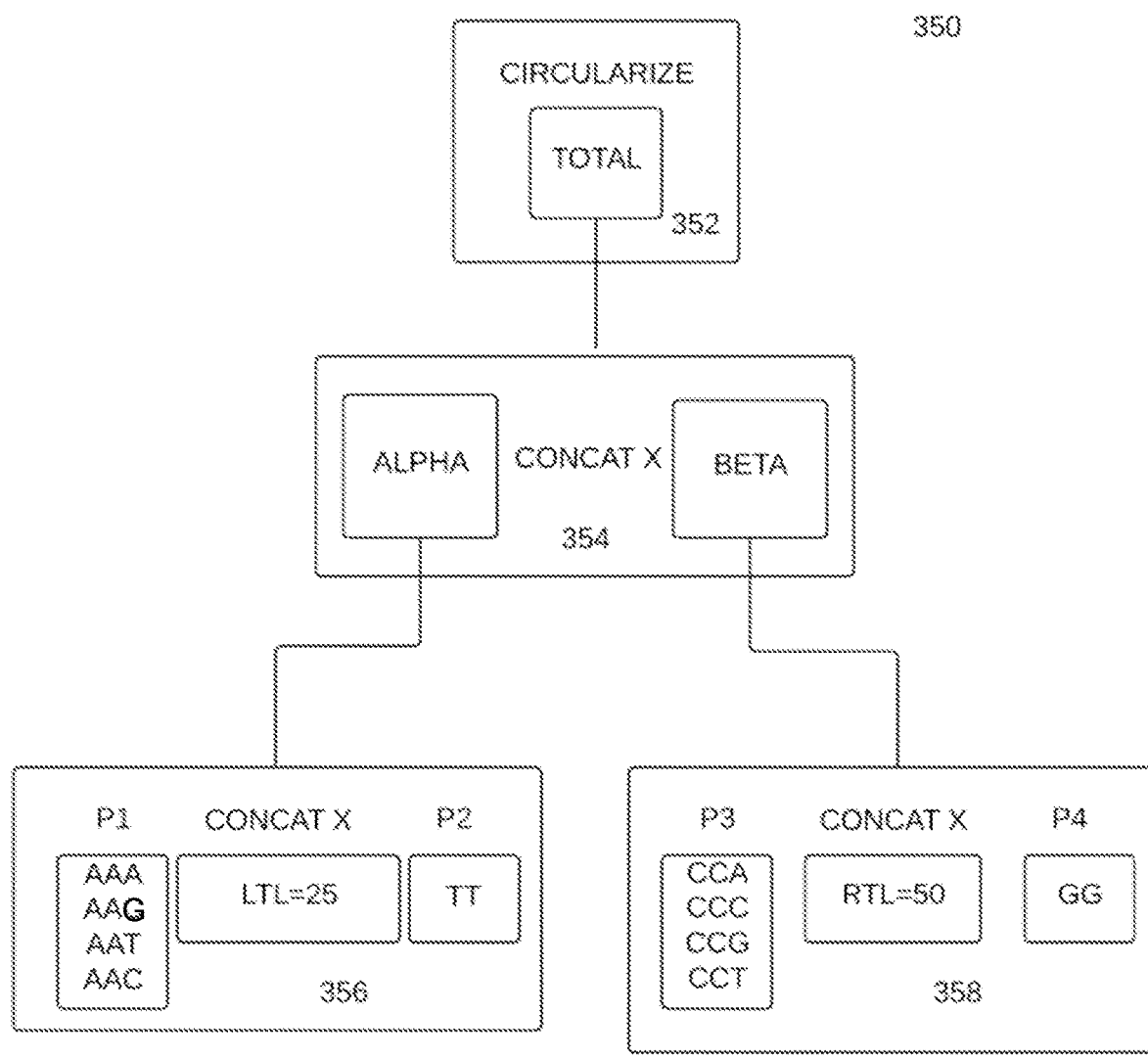
FIG. 3 illustrates an example of a recursive concatenation function enabled by embodiments of the invention.

Referring to FIG. 3, the following is an example of implementation of a recursive concatenation function enabled by embodiments of the invention. Here, recursion refers to the organization of information or functions in levels or layers, where objects contain other similar objects, or the evaluation of a function depends on evaluation of other, similar sub-functions. In this example, the concatenation function, as well as the DNA specification, is recursive.

Before circularization of the output "total" below into plasmid form, the example function in linear form may be expressed as:

```
total = (p1 x p2) x (p3 x p4)
total = alpha x beta,
where alpha = p1 x p2 and beta = p3 x p4, and p1, p2, p3 and p4
represent promoters.
```

Here, the cross product concatenation of alpha and beta is the outer function, where each of alpha and beta represents an inner cross product of two promoters. Note that any of the inputs to the cross product function can be a list of inputs and not just a single input.

To implement this functionality in the programming language of embodiments of the invention, the input interface 202 may receive from the user or another computing device the following script. (In the code below, total is renamed "myplasmid" after circularization, and alpha and beta are, respectively, renamed "left side" and "right side." Thus, my plasmid=circularized (left side×right side).) Also, note that comments in program code may be represented by either "//" or "#" herein.

p1=[dna("AAA"), dna("AAG"), dna("AAT"), dna("AAC")]//a list of promoters, here each represented by a literal string representing three nucleotides p2=dna("TT")//a single (scalar) string representing a promoter p3=[dna("CCA"), dna("CCC"), dna("CCG"), dna("CCT")]//a list of promoters p4=dna("GG")//a single promoter setparam "name", "left side"//Assigns the string value "left side" to the name parameter of the DNA specification that follows setparam ("alpha").

setparam "leftTailLen", 25//Sets the maximum left tail length of alpha to 25 base pairs for PCR amplification at the factory.

alpha=p1×p2//alpha is cross product of p1 and p2 setparam "name", "right side"//Assigns beta the name "right side."

setparam "leftTailLen", 50//Set left tail length of beta to 50 base pairs.

beta=p3×p4//beta is cross product of p3 and p4 setparam "name", "my linear seq"//Assigns total the name "my linear seq"total=alpha×beta//total is cross product of alpha and beta, which themselves are each cross products setparam "name", "my plasmid"//Assigns the name value "my plasmid" to the output of the circularized version of total
out=circularize(total)//circularizes the linear total string into a plasmid representation
create out//specifies that "out" represents a design campaign In this example, the interpreter 204 would populate the DNA specification with the function/operator, inputs and parameters, but would not execute the function to resolve the outputs. The resulting DNA specification "my plasmid" follows below, and is illustrated as a tree data structure 350 in FIG. 3. Note that the myplasmid DNA specification data structure is recursive, including child DNA specifications ("Child DnaSpec"), and that the child DNA specifications, in this example, include DNA components representing the input sequence operands.

```
DnaSpecification:
 Id: 18000000498
 Name: my plasmid
 Description: circularize
 Creating app: codon 1.0.0-SNAPSHOT-477743830d11c9b0fbfaa80cd0ad98c7bc3547ba( )
 Sequence Function: CIRCULARIZE (UNARY) // top-level function (352) (reference numerals refer to Figure 3 tree data structure)
 dnaInputs:
  items:
   Child DnaSpec: id=18000000497 {
    DnaSpecification:
     Id: 18000000497
     Name: my linear seq
     Description: cross product concatenation
     Creating app: codon 1.0.0-SNAPSHOT-477743830d11c9b0fbfaa80cd0ad98c7bc3547ba( )
     Sequence Function: CONCATENATE (CROSS) // (354)
     dnaInputs:
      left: // "left side" = cross product of list [AAA, AAG, AAT, AAC] x TT
       Child DnaSpec: id=18000000496 {
        DnaSpecification:
         Id: 18000000496
         Name: left side
         Description: cross product concatentation
         Creating app: codon 1.0.0-SNAPSHOT-477743830d11c9b0fbfaa80cd0ad98c7bc3547ba( )
         Sequence Function: CONCATENATE (CROSS) // (356)
         dnaInputs:
          left: // the list [AAA, AAG, AAT, AAC], represented by DNA component literal strings
           DnaComponents:
            DnaComponent: id=13000119900 {
             DnaComponent:
              Id: 13000119900
              Name: dna string
              Description: literal: AAA
              Molecular form: LINEAR
              Sequence: AAA
            }
            DnaComponent: id=13000119899 {
             DnaComponent:
              Id: 13000119899
              Name: dna string
              Description: literal: AAG
              Molecular form: LINEAR
              Sequence: AAG
            }
            DnaComponent: id=13000119898 {
             DnaComponent:
              Id: 13000119898
              Name: dna string
              Description: literal: AAT
              Molecular form: LINEAR
              Sequence: AAT
            }
            DnaComponent: id=13000119897 {
             DnaComponent:
              Id: 13000119897
              Name: dna string
              Description: literal: AAC
              Molecular form: LINEAR
              Sequence: AAC
            }
          right: // the scalar TT
           DnaComponents:
            DnaComponent: id=13000119896 {
             DnaComponent:
              Id: 13000119896
              Name: dna string
              Description: literal: TT
              Molecular form: LINEAR
              Sequence: TT
            }
         Parameters:
          leftTailLen: 25
       }
      right: // "right side" = cross product of list [CCA, CCC, CCG, CCT] x GG
       Child DnaSpec: id=18000000495 {
        DnaSpecification:
         Id: 18000000495
         Name: right side
         Description: cross product concatentation
         Creating app: codon 1.0.0-SNAPSHOT-477743830d11c9b0fbfaa80cd0ad98c7bc3547ba( )
         Sequence Function: CONCATENATE (CROSS) //(358)
         dnaInputs:
          left: // the list [CCA, CCC, CCG, CCT]
           DnaComponents:
            DnaComponent: id=13000119895 {
             DnaComponent:
              Id: 13000119895
              Name: dna string
              Description: literal: CCA
              Molecular form: LINEAR
              Sequence: CCA
            }
            DnaComponent: id=13000119894 {
             DnaComponent:
              Id: 13000119894
              Name: dna string
              Description: literal: CCC
              Molecular form: LINEAR
              Sequence: CCC
            }
            DnaComponent: id=13000119893 {
             DnaComponent:
              Id: 13000119893
              Name: dna string
              Description: literal: CCG
              Molecular form: LINEAR
              Sequence: CCG
            }
            DnaComponent: id=13000119892 {
             DnaComponent:
              Id: 13000119892
              Name: dna string
              Description: literal: CCT
              Molecular form: LINEAR
              Sequence: CCT
            }
          right: // the scalar GG
           DnaComponents:
            DnaComponent: id=13000119891 {
             DnaComponent:
              Id: 13000119891
              Name: dna string
              Description: literal: GG
              Molecular form: LINEAR
              Sequence: GG
            }
         Parameters:
          leftTailLen: 50
       }
```

```
Parameters:
   leftTailLen: 50
}
Parameters:
   leftTailLen: 50
```

Assuming no sampling, the execution engine 207 would execute the DNA specification cross product operators on the operands to produce 16 sequences (which may be represented as DNA components):
SEQ ID NO: 1
SEQ ID NO: 2
SEQ ID NO: 3
SEQ ID NO: 4
SEQ ID NO: 5
SEQ ID NO: 6
SEQ ID NO: 7
SEQ ID NO: 8
SEQ ID NO: 9
SEQ ID NO: 10
SEQ ID NO: 11
SEQ ID NO: 12
SEQ ID NO: 13
SEQ ID NO: 14
SEQ ID NO: 15
SEQ ID NO: 16

An advantageous feature of embodiments of the invention is that the order placement engine 208 may employ the DNA specification data structure, such as that above, to inform its generation of a factory order beyond merely providing output nucleotide sequences for the factory 210 to produce. As noted above, the data structure is in the form of a tree, as illustrated in FIG. 3. The order placement engine 208 may traverse the tree structure upwards from the leaves (e.g., corresponding to 356, 358) to the branches to the starting root node (e.g., corresponding to 352) to determine the operations performed at each stage of execution, as well as the inputs, factory workflow and other parameters employed at each stage. The order placement engine 208 may incorporate this information into the factory order. (Note that the "performance" of operations herein may alternately refer to in silico execution of the operations by the execution engine 207 or the interpreter 204 (depending upon the embodiment) or corresponding physical in vivo or in vitro physical reification of the operations in the gene manufacturing system, depending upon the context of the discussion herein, as would be recognized by those skilled in the art. For example, a concatenation operation on two nucleotide sequences would be performed logically by a computer device, whereas it would be physically reified by the joining together of two physical sequences in the factory.)

Thus, unlike conventional sequence design implementations, embodiments of the present invention provide a data structure for sequence design that informs the factory order placer (here the order placement engine 208) of not just the final sequence output, but also operational and contextual information at beginning, intermediate and ending stages of design development. The carrying forward of this information relieves the burden on the factory 210 to determine all beginning and intermediate parts, workflows and other parameters, thus improving the efficiency of production of the desired sequences. For example, based on this information in the DNA specification, the order placement engine 208 may determine the initial base strain to be modified, as well as potentially different promoters, workflows, temperature settings, and primers to be used at the factory 210 at different intermediate stages in the process of assembling the final, desired nucleotide sequence. For example, the tolerated range of annealing temperatures may be different for amplifying from genomic DNA than for amplifying from plasmid DNA.

Figure 4:
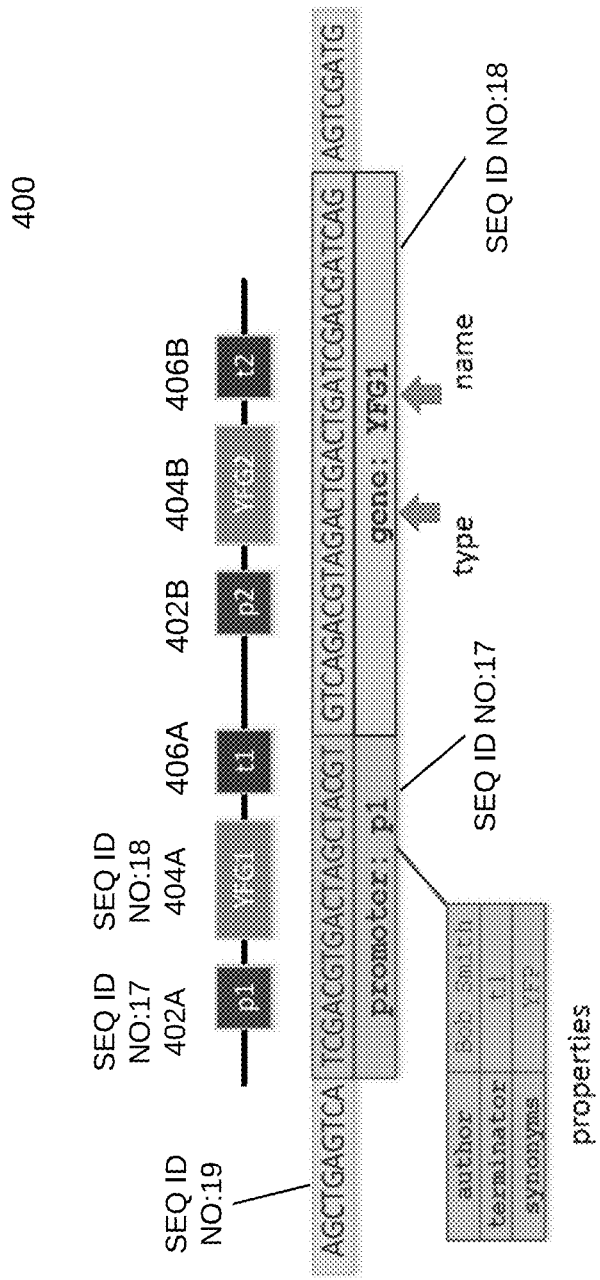
FIG. 4 illustrates an example of an annotated DNA sequence including two sets of promoters, genes, and terminators, according to embodiments of the invention.

The setparam keyword in the DNA specification may be used to set the name and description of any created DNA specifications, as well as other attributes governing how the factory operations are to be performed. The setparam statement takes two arguments, a parameter name, and a value to assign to it. Some parameters use a single string value; others can use a single string or a list of strings. The "name" and "description" parameters will set the most obvious user-visible properties of a DnaSpec. The following is a non-exhaustive list of parameters that can be specified using setparam:

amplifyPart—A boolean value of "true" or "false" to specify whether the part should be amplified.

assemblyMethod—The construction method to use at the factory to assemble the constructs. E.g., one of "yeast homologous recombination", "gibson", or "LCR"

description—The description to assign to the DnaSpec/campaign.

groupName—The name to assign to the collection of assembly parts produced by a particular DnaSpecification. May be used in conjunction with amplifyPart.

leftTailLen and rightTailLen—Integer values specifying the maximum tail length to generate for amplification name—The name to assign to the DnaSpec/campaign.

notes—A longer free-form set of notes about the campaign for human reference. This may be a list of strings.

outputName—A string or list of strings specifying the names to assign the DnaComponents that are generated by the DnaSpec created with this parameter name. (e.g., if you are circularizing a set of inputs, you can setparam "outputName", ["myCircular1", "myCircular2",] to name the different circularized constructs.

primerSource—E.g., one of "IDT" (Integrated DNA Technologies, Inc.) or "library", to specify the source of primers for a campaign plasmidSource—E.g., one of "build" or "library" to specify source of plasmids for a campaign targetAnnealingTemperature—The desired temperature to be employed at the factory to amplify a construct Replacement Function Another particularly pertinent function is the replacement function. As an example of a program to replace the promoters located before genes in the DNA sequence of a microbial strain, refer first to the DNA component of FIG. 4. FIG. 4 illustrates an example of an annotated DNA sequence 400 including two sets of promoters 402A, 402B, genes 404A, 404B, and terminators 406A, 406B (generically "p-g-t" sequence), respectively p1(SEQ ID NO: 17)-YFG1(SEQ ID NO:18)-t1 and p2-YFG2-t2. (Annotation is shown for promoter p1(SEQ ID NO: 17) and gene YFG1 (SEQ ID NO: 18).)

Figure 5:
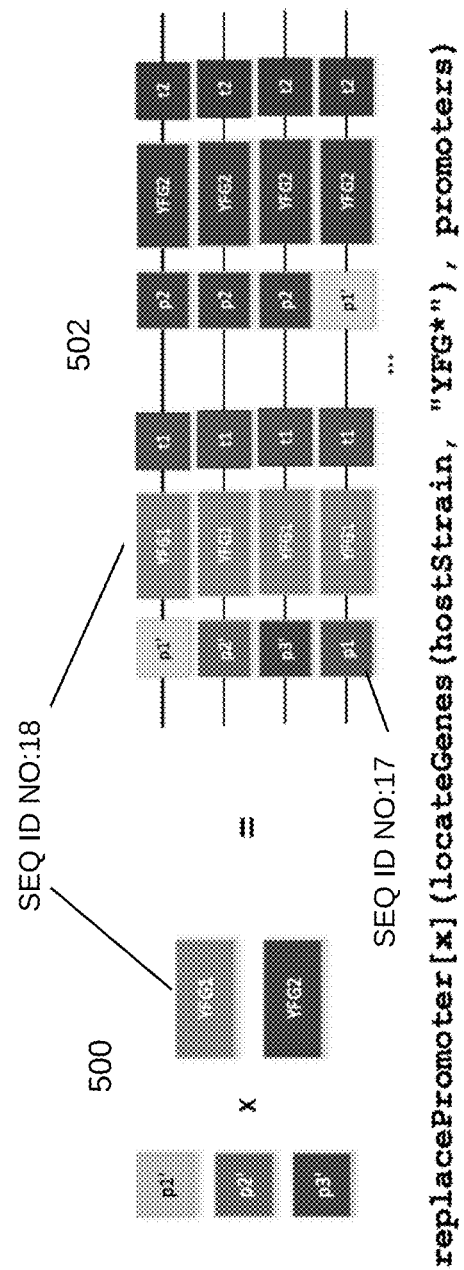
FIG. 5 illustrates a promoter swap operation applied to the sequence of FIG. 4, according to embodiments of the invention.

FIG. 5 illustrates a promoter swap operation 500 applied to the p-g-t sequence of FIG. 4. Using the combinatorial cross-product ("x") operation, the program will generate all combinations of all p-g-t sequences with the promoters in the original p-g-t sequence replaced one-by-one with p1', p2' and p3', resulting in six output sequences to be converted into a design campaign. (The first four output sequences 502 are illustrated in the figure.)

The program code for performing this operation follows. Descriptions of the functions are given in the comments.

```
hostStrain = dnaForStrain(
    "e-coli-461") # Load the DnaComp associated with the strain with the
specified ZId or name.
promoters = load("promoter-lib-2-13-2015.gb") # Load from the LIMS
library all promoters identified by the name in the argument.
genes = locateGenes(hostStrain, "YFG*") # Locate the genes whose
names begin with "YFG" in the microbe strain identified by hostStrain
variable, and assign this Located DnaSpecification the name "genes.
("YFG*" stands for "Your Favorite Gene," a placeholder for a user's
preferred descriptive name within a particular application instance.)
create replacePromoter[x](genes, promoters)
```

The replacePromoter( ) function replaces the promoter annotated as regulating a given gene. As indicated by the cross-product function call modifier "x", replacePromoter( ) here generates representations of all annotations (locations in the genome) identified by "genes" with representations of the genes' annotated promoters replaced by representations of promoter sequences identified by "promoters." This create function generates a DnaSpecification with a "replace" function, and parameters indicating that it should be performed in "replace-promoter" mode, that one argument list is the promoters, and the other argument list is Located DnaSpecification (here "genes"), i.e., one or more DnaSpecifications whose function is "locate," and indicates the collection of genes by name whose promoters should be swapped. The "create" function creates a design campaign for input to the factory for generation of DNA sequences.

One feature of embodiments of the invention is that the genomic design language includes genome-aware edit operations. For example, the interpreter 204 (or in some embodiments, the execution engine 207) executes replacePromoter( ) to obtain knowledge of the location of the promoter annotated as regulating the gene in the p-g-t sequence. By reading the p-g-t sequence in the library, the interpreter 204 (or in some embodiments, the execution engine 207) identifies the appropriate promoter for each gene from its DNA component annotations, and then enables replacement of the promoter. See *BBF RFC 108: Synthetic Biology Open Language (SBOL) Version* 2.0.0, editors Bartley, et al., Jul. 31, 2015 (annotations).

Note that replacePromoter( ) does more than use promoter annotations to locate the promoter regulating a gene. It replaces the whole sequence from the upstream end of the annotated promoter to the start codon of the gene. If no promoter annotation exists for a gene of interest, the new promoter will be inserted before the gene. If there are annotations that overlap the region of the promoter, the method will warn the user or sometimes try to rectify the collision.

Figure 6:
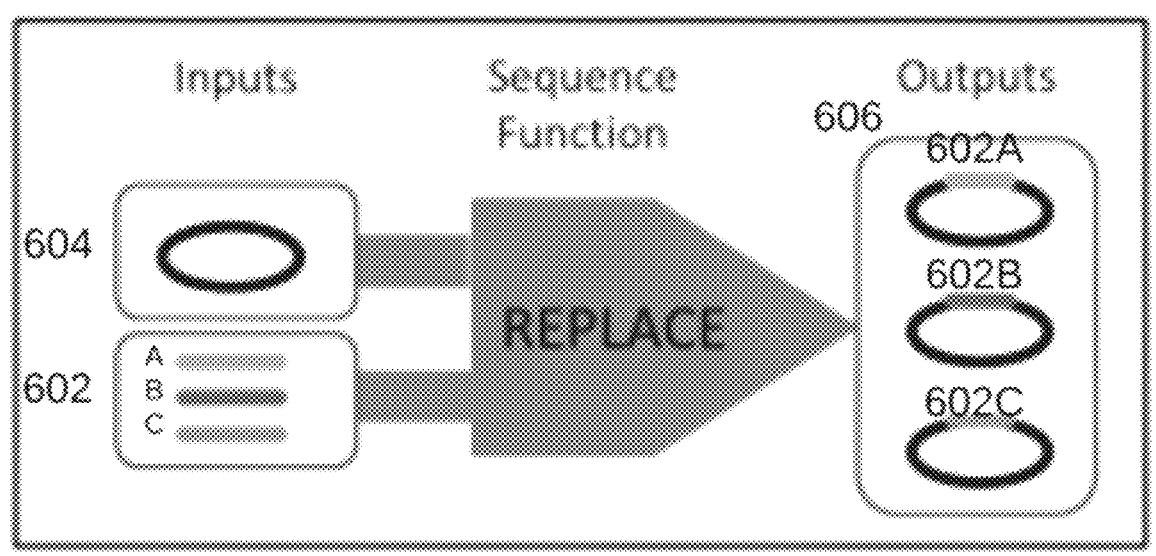
FIG. 6 provides a graphical representation of a DNA specification of a replace-locate cross-product function, according to embodiments of the invention.

FIG. 6 provides a graphical representation of a DNA specification of a replace[x](locateTerm[x](plasmids, "insertion-site"), newGenes) cross-product function for inserting genes (newGenes) 602A, 602B, 602C into a plasmid 604 by representing all three combinations 606 of the plasmid with its insertion region replaced with the specified genes 602A, 602B, 602C. The function takes the cross-product of the list of genes with the plasmid insertion region (which could be represented by a scalar DNA component) to output a DNA specification representing the modified plasmids. Alternatively, the plasmids may be represented as DNA components. The function first specifies the location within the plasmid of the sequence to be replaced by calling locateTerm [x] (plasmids, "insertion-site"). Alternatively, the insertion site may be located by identifying the name of the site location, e.g., locateName[x](plasmid, "MseI cut site"). These functions return LocatedDnaSpecifications. The replace function then performs the cross-product replacement of the list of newGenes into the locations specified by the LocatedDnaSpecifications.

The examples above demonstrate another advantage of the recursive capabilities of the programming language and data structures of embodiments of the invention. The language enables the user to independently control all stages of the sequence manufacturing process (beginning, intermediate, and end) by specifying the operations, inputs and conditions to be used at each stage of manufacture. In the example above, the specification specifies cross product operations at different levels (nodes) of the DNA specification tree structure: a cross product operation at the location resolution inner function, as well as at the replace function outer function further up the tree structure. Similarly, the user may have specified, at different stages/levels, different combinations of dot and cross operators, different parameters (e.g., temperature and other environmental conditions), and different inputs (e.g., promoters).

Non-Deterministic Functions

Embodiments of the invention provide probabilistic, non-deterministic functions, some of which reflect real-life results of laboratory methods that create stochastic results. In general, a probabilistic function effects changes to a nucleotide sequence in a non-deterministic manner. Examples are insertion of a transposable element at random locations of a sequence, one or more single nucleotide changes anywhere in the sequence (e.g. reflecting chemical or UV mutations), one single nucleotide change at the third position of any one codon in a coding sequence (e.g., through the production of an NNK library), one or two nucleotide changes at known locations (e.g., from PCR with degenerate primers), or an unknown set of changes via directed evolution.

The two examples below implement probabilistic functions enabling constrained randomization in the generation of nucleotide sequences.

```
# Define the starting sequence
enzyme_seq = dnaComponent(13000000000)
sequence_library = mutate(enzyme_seq, "NNK") # mutate the given
sequence using the NNK pattern (i.e., change the third base "K" of each
codon, with K restricted to a randomized selection of either guanine (G)
or
thymine (T))
# Another example to create a degenerate primer
base_primer = dnaComponent(13000000001) # a template sequence for
the primer set
variable_locations = locate(base_primer, [4, 9]) # identify positions 4
and 9 as those to vary
degen_primers = degenerate(variable_locations, ["A", "G", "C", "T"])
# create the full set of possible primers whose base at positions 4 and 9
could be any of A, G, C, or T selected randomly.
```

Creating a Plasmid

As another example, the following program loads some promoters, some genes, a terminator and a plasmid backbone. Using the cross-product concatenation function, the program will create all possible combinations of promoters and genes (and the terminator), hook them each to the backbone, circularize them into a plasmid, and create a campaign that represents all these designs:

```
# Get the parts ready:
promoters = dnaSpecification(18000000001)
genes = dnaSpecification(18000000002) # id for YFG
# (a gene denoted by "your favorite gene (YFG)") goes here.
```

```
terminator = dnaComponent(13000000001)
plasmidBackbone = dnaComponent(13000109030)
# Create the P-G-T sequences. We want all possible combinations of
promoters and genes, so we use the 'x' (concatenate
cross-product) operator.
# Since we have only one terminator, and one backbone, and we want
them applied to all
sequences, we use 'x' again:
assemblies = promoters x genes x terminator
prePlasmids = assemblies x plasmidBackbone
# We don't want linear DNA, we want to circularize the preplasmids to
generate circular plasmids.
plasmids = circularize(prePlasmids)
# Specify that the 'plasmids' DnaSpec is the final campaign.
# This will upload the generated DnaSpec to LIMS.
create plasmids
```

Sampling

As discussed above, synthetic biology systems such as those of embodiments of the present invention enable multiple operations to be performed on multiple DNA parts, represented by multiple DNA operands. Thus, the resulting design campaign may include representations of many thousands of DNA sequences. For example, a program may generate 10,000 modified genomes, which would occupy on the order of 50-100 GB of storage space. This information would not enable efficient management in a typical conventional memory at this time, and would instead require, for example, slower disk-based access. Current commercial computer systems cannot load and operate efficiently on a 50-100 GB SBOL file representing genomes. Such operations may crash or cause unacceptable delays in processing.

Embodiments of the invention avoid these potential storage and processing problems by sampling. In some embodiments, the order placement engine 208 may select only a subset of the outputs for incorporation into a factory order. This operation may employ many different techniques, such as, for example, random sampling to produce N constructs, or sampling the first or last K DNA constructs. To reduce storage requirements, this approach may store only the sampled outputs for incorporation into the factory order.

Alternatively, in embodiments in which the execution engine 207 executes the DNA specification to generate outputs that populate the DNA specification, the execution engine 207 itself may optionally sample the DNA specifications from the interpreter 204 to select a subset of DNA specifications for execution. This approach is particularly applicable to DNA specifications representing intermediate operations (e.g., child DNA specifications) within the larger, recursive DNA specification output data structure of the interpreter 204. As a result, the execution engine 207 produces outputs only for the selected, executed DNA specifications. Decoupling of interpretation by the interpreter 204 from execution by the execution engine 207 enables sampling-for-execution to reduce the size of the output by many orders of magnitude, thereby reducing the need for very large storage capacity and heavy processing.

The sampling operation of the embodiments immediately above may employ many different techniques, such as, for example, random sampling, or sampling the first or last K DNA specifications for execution. In addition, the execution engine 207 may more intelligently sample the DNA specification before execution. One approach is to weight DNA specifications for execution. For example, within the DNA specification data structure, promoters and other parameterized factors may be assigned different weights depending upon, e.g., their cost, availability, or known effectiveness.

For example, assume a DNA specification data structure applies a concatenate cross product function to two input operands—a list of genes and a list of promoters. In this example, each promoter may be assigned weighting parameters (params) between 0 and 1 that would inform the execution engine 207 in its selection of DNA specifications to execute. The higher the weight of a promoter in the list, the more likely the execution engine 207 will execute the DNA specification for (apply the concatenate cross product operator to) such promoters.

The weights can themselves be added as parameters of a DNA specification to weight other parameters. For example, a child DNA specification (i.e., below the top-level DNA specification) may include a weighting parameter assigned a probabilistic weight expressed as weightPromoter=$p_i$ for a single promoter within the child DNA specification, or weightPromoter=$[p_1, p_2, \ldots pN]$ for a list of promoters within the same child DNA specification. The sum of the weights for the parameters (e.g., promoters) may add up to a value of 1, particularly for parameters at the same level of operations within the hierarchical tree structure of a recursive DNA specification.

Another strategy would be to employ a design-of-experiments methodology to intelligently select only a specified number of the possible promoter-gene combinations in order to learn the efficacy of each. As part of this implementation, the execution engine 207 may, in one embodiment, execute the appropriate specifications to ensure that each promoter is used at least once in a combination, while limiting the total number of combinations.

Even DNA components can be weighted to guide the execution engine 207 in its execution of operators on the DNA components. For example, a DNA specification having a list of DNA components as inputs may include a weight vector weightVector=$[p_1, p_2, \ldots pN]$ for the list of DNA components.

Caching

In embodiments of the invention, the execution engine 207 (or the interpreter 204 in embodiments in which the interpret executes DNA specifications) may employ caching to avoid the recalculation of results that may be re-used during execution of a DNA specification. For example, a specification may specify the cross product concatenation A×(B×C), where A, B, C are long lists of nucleotide sequences. The execution engine 207 would concatenate each element of A with all the elements resulting from the cross product B×C. It would be redundant and time consuming to recalculate B×C outputs for each concatenation with each item in A, so the execution engine 207 may instead cache those B×C results after the first computation of B×C, and then use those results in the cross product computations with the elements of A. Caching thus saves processing time and increases processing speed Caching finds use not just within the same run (e.g., generation of the order), but across different runs. For example, the user may determine that better or different results are desired compared to the sequences generated from a previous order. Accordingly, the user may re-run a program to place another factory order, perhaps this time directing sampling to select a different subset of DNA specifications to execute. In doing so, however, the script may still require execution of some of the same intermediate operations as prior order generation runs. With reference to the example herein of nested concatenation of right and left side promoters, a user may want to rerun the higher-level (total) concatenation function to obtain different right-side sequence outputs, but not change the left-side operations.

Thus, the system may cache the lower-level, intermediate left-side results for later use during the re-running of the higher-level function. In general, outputs of lower-level operations (e.g., at the leaves of the hierarchical tree structure) would be needed more repeatedly than higher-level operations, so the execution engine 207 may favor caching lower-level outputs over those from higher levels if storage is constrained. Based on the foregoing, the execution engine 207 in embodiments of the invention caches DNA specification results from different levels of operations within the tree structure to avoid re-execution during subsequent runs, thus saving processing time and increasing processing speed.

Computer System

FIG. 7 shows an example of a computer system 800 that may be used to execute program code stored in a non-transitory computer readable medium (e.g., memory) in accordance with embodiments of the present invention. The computer system includes an input/output subsystem 802, which may be used to implement input interface 202 to interface with human users and/or other computer systems depending upon the application. For example, the editor of embodiments of the invention may be implemented in program code on system 800 with I/O subsystem 802 used to receive input program statements from a human user (e.g., via a GUI or keyboard) and to display them back to the user. The I/O subsystem 802 may include, e.g., a keyboard, mouse, graphical user interface, touchscreen, or other interfaces for input, and, e.g., an LED or other flat screen display, or other interfaces for output. Other elements of embodiments of the invention, such as the order placement engine 208, may be implemented with a computer system like that of computer system 800, perhaps, however, without I/O.

Program code may be stored in non-transitory media such as persistent storage 810 or memory 808 or both. A processor 804 reads program code from one or more non-transitory media and executes the code to enable the computer system to accomplish the methods performed by the embodiments herein, such as those represented by the flow chart of FIG. 2. Those skilled in the art will understand that the processor may ingest source code, such as statements expressed in the high-level genomic design language of embodiments of the invention, and interpret or compile the source code into machine code that is understandable at the hardware gate level of the processor. A bus couples the I/O subsystem 802, the processor 804, peripheral devices 806, memory 808, and persistent storage 810.

Those skilled in the art will understand that some or all of the elements of embodiments of the invention, such as those shown in FIG. 1 (e.g., interpreter, execution engine, order placement engine, factory, test equipment, analysis equipment), and their accompanying operations, such as those shown in FIG. 2, may be implemented wholly or partially on one or more computer systems including one or more processors and one or more memory systems like those of computer system 800. Some elements and functionality may be implemented locally and others may be implemented in a distributed fashion over a network through different servers, e.g., in client-server fashion, for example.

While the present invention has been particularly described with respect to the illustrated embodiments, it will be appreciated that various alterations, modifications and adaptations may be made based on the present disclosure, and are intended to be within the scope of the present invention. While the invention has been described in connection with the disclosed embodiments, it is to be understood that the present invention is not limited to the disclosed embodiments but, on the contrary, is intended to cover various modifications and equivalent arrangements included within the scope of the claims.

Appendix 1: Function Reference

This appendix describes some of the available functions in the built-in library for the Codon language in the LIMS.

circularize circularize(input: DnaInput) -> DnaSpec circularize(input: DnaInput, originShift: Int) -> DnaSpec Returns a DnaSpec representing the circularized forms of the DNA input(s). If originShift is specified, this shifts the origin downstream (with wrap-around) by originShift base pairs, concat concat[x](left: DnaInput, right: DnaInput) -> DnaSpec Concatenates the left and right arguments. Function-call synonym for left * right or left x right depending on the operator modifier chosen.

dna dna(dnaSeq: String) -> DnaComp dna(dnaSeq String, name: String) -> DnaComp

Returns a DnaComponent encapsulating the DNA sequence represented by the specified string. You may optionally specify a name for the created DnaComponent.

ecoRV=dna("GATATC") # Define an enzyme binding site ecoRV2=dna("GATATC", "ecoRV") # . . . Create a named DnaComponent.

dnaComponent dnaComponent(zid: Int) -> DnaComp dnaComponent(name: String) -> DnaComp Connect to LIMS library and load the DnaComponent with the specified ZId or name my DnaComponent=dnaComponent(13000000001)

dnaForStrain dnaForStrain(zid: Int) -> DnaComp dnaForStrain(name: String) -> DnaComp Load the DnaComp associated with the strain with the specified ZId or name. . . . . . . . . . . . . . . .

baseStrainDna=dnaForStrain(7000000001)

dnaSpecification dnaSpecification(zid: Int) -> DnaSpec dnaSpccification(name: String) -> DnaSpec Connect to LIMS and load the DnaSpecification with the specified ZId or name.

myDnaSpec=dnaSpecification(18000000001)

hello hello(name: String) -> String

Returns a friendly greeting to the specified name. As you might imagine, this is mostly useful for playing around.

print hello("Bob") # prints "Hello, Bob" to the screen len len(list: List[Any]) -> Int len(map: Map[Any])->Int len(str: String) -> Int Return the length of the specified list, map or string.

listSpec listSpec(lst: List[DnaComp]) -> DnaSpec listSpec(lst List[DnaSpec]) -> DnaSpec Take a list of DnaComps or DnaSpecs and create a DnaSpec that enumerates these inputs.

See also: partsList( )

partsList partsList(parts: List[DnaInput], groupName: String) -> DnaSpec partsList(parts: List[DnaInput], groupName: String, leftLen: Int, rightLen: Int) -> DnaSpec Creates a DnaSpec representing a parts list with the specified properties. The output DnaSpec
will have the groupName property set according to the argument. If left and right tail lengths
are not provided, then they will be set to zero in the DnaSpec. Otherwise, the specified left
and right tail lengths will be used. The parameters for groupName, leftTailLen and
rightTailLen specified by any prior setparam statements will be ignored.
Using this function is equivalent to the following:
myParts=[ . . . ]# Set to a list of DnaSpecs, DnaComps, etc.
setparam "amplifyPart", "true"
setparam "groupName", myGroupName
setparam "leftTailLen", myLeftLen
setparam "rightTailLen", myRightLen
myPartsList=listSpec(myParts)
clearparams # or otherwise revert amplifyPart/groupName/leftTailLen/rightTailLen
See also: lislSpec( ).
toSeq
toSeq(dna: DnaComponent) -> String
Return the DNA sequence underlying a DnaComponent as a string.
toString
toString(val: Any) -> String
toString(val: Any, recursive: Int) -> String
Converts the specified value to a string. The recursive argument is a boolean flag (use
constants true or false) to indicate whether DnaSpec structures should be recursively looked
up.
print toString(foo) # Print the value of 'foo' to the output.
print toString(myDnaSpec, true) # Print an entire DnaSpecification and its children
proswp
proswp[x](baseStrain: LocatedDnaSpec, promoters: DnaInput)-> DnaSpec
proswp[x](baseStrain: LocatedDnaSpec, promoters: DnaInput, allowdnsert: Int) -> DnaSpec
Performs the promoter swap associated with inserting the specified promoter(s)
immediately upstream of the genes identified in located baseStrain,
replacing the previous driving promoter.
If 'allowInsert' is specified, this should be 'true' to allow insertion of
promoters if no existing promoter is driving the specified gene, or 'false' to
fail if no driving promoter exists to replace.
replace
replace[x](baseStrain: LocatedDnaSpec, insertions: DnaInput) ->
At the specified location(s) of the base strain(s), replace the subsequence identified
in the location with the new sequences specified by 'insertions'.
You may specify multiple insertions in 'insertions'. Depending on whether the
cross ('[x]') or dot ('[*]') operator is chosen, this will place one insertion
in each yielded location in 'baseStrain', or apply each insertion to each
possible location.

The replacement operation may specify a strict insertion operation that replaces an empty
replaceable region with the replacement sequence part "insertions". Alternatively, the
replacement operation may specify a strict deletion operation that replaces the replaceable
region with an empty replacement sequence part.
locate, locate.Name, locate Term
locate(baseStrain: DnaInput, offset: Int) -> LocatedDnaSpec
locate[x](baseStrain: DnaInput, offset: List[Int]) -> LocatedDnaSpec
locate(baseStrain: DnaInput, offset: Int, length: String) -> LocatedDnaSpec
locate[x](baseStrain: DnaInput, offset: List[Int], length: List [String]) -> LocatedDnaSpec
locate(baseStrain: DnaInput, offset: Int, subseq: String) -> LocatedDnaSpec
locate[x](baseStrain: DnaInput, offset: List[Int], subseq: List [String])-> LocatedDnaSpec
locateName(baseStrain: DnaInput, annotationName: String) -> LocatedDnaSpec
locateName[x](baseStrain: DnaInput, annotationNames: List[String])-> LocatedDnaSpec
locateTerm(baseStrain: DnaInput, annotationTerm: String) -> LocatedDnaSpec
locateTerm[x](baseStrain: DnaInput, annotationTerms List [String])-> LocatedDnaSpec
Given some DnaInput, return a LocatedDnaSpec that wraps around it. The
LocatedDnaSpec contains the same outputs, but with location information about the
identified region returned in an output parameter TheLocatedDnaSpec is a DnaSpecification
whose function is LOCATE. The region identification is made via the parameters map within
the DnaSpecification.
The location can be either a single base, or a region extending over many bases.
The location is specified as either a single offset, or a region extending from
'offset' to 'offset+length', or 'offset+len(subseq)'. In the latter case,
'subseq' must be the exact-matching DNA sequence starting at 'offset'.
A location can also be given as the (unique) name of an annotated region in
each base strain element. The located region is the entire extent of the
annotation.
If multiple annotations or offset/offset+length/offset+subseq values are given,
then these are applied one-at-a-tinie to individual elements of 'baseStrain', or
all applied to all elements of 'baseStrain' depending on whether the dot ('[*]')
or cross ('[x]') operator is chosen, respectively.
Annotation-based locations can be specified as either a specific annotation name
to return (in which case they should return a single location per input genome)
or the annotation's sequence feature term name (in which case, many locations per
input genome may be returned).
A LocatedDnaSpec can be used as the input to functions such as 'insert', 'replace',
and 'delete'. When removing bases from the DNA sequence (e.g., as in 'replace' and 'delete'), the amount to remove is specified as a parameter to 'locate( )',
either in a number of base pairs, or in the specific subsequence to remove. That
is, the entire located region is removed by 'replace' or 'delete'.
You may specify an empty subsequence or a length of 0 to indicate no deletion
(e.g., the 'replace( )' function is being used for pure insertion).
Offsets begin at 1 and run up to and including '|the DNA sequence|'. Consider
the following example: . . .
input=dna("AATTCG")
replace[x](locate(input, 3, 1), dna("A"))//Returns "AAATCG". . .
insert
insert[x](baseStrain: LocatedDnaSpec, insertions: DnaInput) -> DnaSpec
At the specified locations of the base strain, insert the specified insertions.
If the 'baseStrain' or 'insertions' are multiple inputs, then the insertions
are performed in a dot or a cross product with the elements of 'baseStrain'
per the function call modifier.
insertDownstream
insertDownstream[x](baseStrain: LocatedDnaSpec, insertions: DnaInput) -> DnaSpec
Inserts the DNA specified by 'insertions' immediately after the specified
annotation in the base strain, relative to the direction of the annotation. That
is, in a "forward" annotation, inserts to the right of the annotated sequence
(as read from 5' to 3'); in a reverse annotation, inserts to the left.
If the baseStrain or insertions DnaInputs represent multiple inputs, the
insertions are made as a dot or cross product of all 'baseStrain' instances with all
'insertion' instances per the function call modifier.
insertUpstream
insertUpstream[x](baseStrain: LocatedDnaSpec, insertions DnaInput) -> DnaSpec
Inserts the DNA specified by 'insertions' immediately before the specified
annotation in the base strain, relative to the direction of the annotation. That
is, in a "forward" annotation, inserts to the left of the annotated sequence
(as read from 5' to 3'); in a reverse annotation, inserts to the right.
If the baseStrain or 'insertions' DnaInputs represent multiple inputs, the
insertions are made as a dot or cross product of all 'baseStrain' instances with all 'insertion'
instances per the function call modifier.

```
protocol ZymergenAvroDna {
    // Records and types describing the storage of DNA sequences in
    // DnaComponents.
    /**
     * The specific way this DnaComponent's sequence is encoded; used to
     * determine which fields of the type-discriminated union
    that is DnaComponentStorageAvro
     * are valid.
     */
    enum StorageMethod {
        LITERAL,
        DIFF
        // Other storage mechanisms could be added later; e.g. SUBSTRING
    }
    /**
     * Specifies a single diff in a StorageMethod.DIFF storage.
     *
     * <p>Replaces "existingData" beginning at 0-indexed offset "startPoint" into the
     * parent with the text found in "newData".
     */
    record DnaStorageDiff {
        long startPoint;
        string existingData;
        string newData;
    }
    /**
     * Structure that holds an encoded form of the sequence associated with a DnaComponent.
     *
     * <p>Different sets of fields are valid in any given DnaComponentStorageAvro based on
     * the value of <code>storageMethod</code>.
     */
    record DnaComponentStorageAvro {
        // Particular methodology used to encode this storage object.
        StorageMethod storageMethod;
        // Fields for StorageMethod.LITERAL.
        union { null, string } literalString = null;
        // Fields for StorageMethod.DIFF.
        union { null, long } diffParentZId = null;
        union { null, array<DnaStorageDiff> } diffItems = null;
    }
    // Other types associated with DnaComponent.
    enum Direction }
        FORWARD,
        REVERSE
    }
    /* Defines a region of dna sequence */
    record RegionAvro {
        long startPosition;
        long endPosition;
        Direction direction = "FORWARD";
    }
    /* Defines a specific region of dna as being of a type.
    */
    record DnaAnnotationAvro {
        long creatorId = 0; // to be set when created
        long createTimestamp = 0; // to be set when created
        string annotationName;
        string description;
        long featureTermId = 0; // the id in the feature table
        string featureTerm; // the name of the feature, will be used to lookup id
        RegionAvro position; // where this annotation is in the seq
        union { null, map<array<string>> } properties = null;
        boolean canceled = false;
    }
    enum MolecularForm }
        CIRCULAR,
        LINEAR,
        SINGLE_STRAND // assumed to be linear
    }
    record DnaComponentAvro }
        long id = 0;
        union { null, long } creatorId = null;
        union { null, long } createTimestamp = null;
        string @aliases("name"+) componentName;
        union { null, string } description = null;
        // Preferred mechanism for storing DNA sequences.
```

```
        union { null, DnaComponentStorageAvro } sequenceStorage
    = null;
        union { null, string } sequence = null; // DEPRECATED:
    Should be left null.
        MolecularForm molecularForm = "LINEAR";
        boolean canceled = false;
        union { null, array<DnaAnnotationAvro> } annotations =
    null;
        union { null, map<array<string>> } properties = null;
    }
    // Begin DnaSpecification related records
    // A DnaComponent expressed either as a ZID or as an
    actual DnaComponent
    // object. At least one of zid and component must be non-
    null
      record DnaComponentRef }
        union { null, long } zid = null;
        union { null, DnaComponentAvro } component = null;
    }
    // An input to a DnaSpecification's operations. The name
    of this DnaSpecInput
    // will be held as a key in the dnaInputs map. One of
    dnaComponents
    // or childSpecification must be non-null.
      record DnaSpecInput {
        // A list of literal DnaComponents to operate on.
        union { null, array<DnaComponentRef> } dnaComponents =
    null;
        // Or, a recursive subdefinition of more DNA to
    assemble through the
        // DnaSpecification process.
        union { null, long } childSpecId = null;
        // Or, a recursive subdfn of more DNA to assemble
    through a list of
        // DnaSpecifications
        union { null, array<long> } childSpecIdList = null;
    }
      enum SequenceFunction }
        LIST,              // return all DnaComponents in this
    Specification
        REPLACE,           // replace subsequence A at location B
    with sequence C
        CONCATENATE,       // sequence A + B
        SUBSTRING,         // A[x:y]
        CIRCULARIZE,       // turn a linear molecule into a circular
    one
        LOCATE,            // find a region of input sequences
        CUT,               // Demarcate cut point for future
    edits/insertions.
        ALIGN,             // Align to a specific feature
        FILTER,            // Retrieve a subset of inputs via various
    conditions
        SAMPLE             // Sample the inputs with properties for
    replacement & probability
    }
      enum FunctionModifier }
        UNARY,
        ZIP,               // iterate as for i: A[i], B[i]
        CROSS              // iterate as for i: for j: A[i], B[j]
    }
    // The specification of the actual logical operation to
    perform on
    // the DNA inputs. This specifies a language-level
    operation
    // ("concatenate", "splice", etc.) rather than a physical
    operation
    // ("ligate", "PCR")
      record DnaSequenceFunctionAvro }
        // The name of the function to perform. "splice"
        union { null, SequenceFunction } functionName = null;
        // The way to combine parameter lists
        union { null, FunctionModifier } functionModifier =
    null;
    }
    // The test criteria to establish that a sample contains
    the correct DNA
    // sequence.
      record QcTestAvro }
        string testName = ""; // e.g. Mse-digest
        string testMethod; // (see below)
        union { null, map<string> } parameters = null; // e.g.
    tolerance, 15%
    // e.g.
    gradient min, 10
    }
    // example test methods: sequence, length, od, alignment,
    colony characteristics,
    // microscopy, control-sample behavior
    // The top-level DnaSpecification object.
      record DnaSpecificationAvro }
    long id = 0;
        union { null, string } name = null;
        union { null, string} description = null;
        union { null, long } creatorId = null;
        union { null, long } createTimestamp = null;
        union { null, string } creatingApp =null;
        union { null, string } creatingAppVersion = null;
        union { null, string } creatingAppParams = null;
        // All dna components and/or dna specifications to
    operate
        // on. The key in this map is the "role" of that
    sequence or set
        // of sequences; the value is what to operate on.
        union { null, map<DnaSpecInput> } dnaInputs = null;
        // A set of named function parameters such as locations
    to replace
        // or splice. The specific function parameter names are
    particular
        // to the sequenceFunction, below.
        union { null, map<array<string>> } parameters = null;
        // A set of named values to be associated with the
    outputs.
        // Array length must be the same as the number of
    outputs.
        union { null, map<array<string>> } outputParameters =
    null;
        // The logical sequence function to apply to the
    dnaInputs.
        union { null, DnaSequenceFunctionAvro }
    sequenceFunction = null;
        // The outputs of the DnaSpecification can be reified
    in the following
        // array. When a DnaSpecification is used as an input
    to another
        // DnaSpecification the DnaComponents it emits will be
    from this array of
        // outputs.
        union { null, array<DnaComponentRef> } dnaOutputs =
    null;
        // A description of the standards by which the
    dnaOutputs will be deemed
        // correct. Each standard is one assay to be performed
    on all of the outputs
        // of this specification and the
    parameters/tolerances/criteria to use as
        // acceptance. Standards are stored by name.
        union { null, array<QcTestAvro> } qcStandards = null;
    }
}
```

What is claimed is:

1. A method for controlling production of engineered host cells, the method comprising:
   (i) receiving, at a computing device, an expression indicating an operation on a first sequence operand and a second sequence operand, wherein sequence operands represent nucleotide sequence parts, the first sequence operand represents a plurality of nucleotide sequence parts, and the second sequence operand represents at least one nucleotide sequence part;
   (ii) executing, by a computing device, instructions to evaluate the expression to a sequence specification, wherein the sequence specification comprises a data structure representing (a) the first and second sequence operands, (b) one or more first-level operations to be performed on one or more first-level sequence operands, and (c) one or more second-level operations, the execution of at least one of which resolves a plurality of values of at least one of the one or more first-level sequence operands, wherein the sequence specification represents genetic modifications; and (iii) generating a factory order based upon execution, by a computing device, of one or more of the first-level operations and one or more of the second-level operations, wherein:

(iv) based on the factory order, nucleotide sequence parts are assembled into a plurality of nucleotide sequences; and (v) the plurality of nucleotide sequences are introduced into a plurality of host cells to produce a plurality of engineered host cells having a plurality of phenotypes that are based upon the genetic modifications represented by the sequence specification.

2. The method of claim 1, wherein:
a subset of the plurality of engineered host cells is selected based on assayed phenotypic performance of the plurality of engineered host cells within the subset;
genetic modifications are selected based on correlations between genetic modifications represented in the sequence specification and assayed phenotypic performance of engineered host cells;
a second plurality of nucleotide sequences is assembled based upon performing (i)-(iv) with the first and second sequence operands, the one or more first-level operations, and the one or more second-level operations being based on the selected genetic modifications; and
the second plurality of nucleotide sequences are introduced into the subset of engineered host cells.

3. The method of claim 1, wherein: the data structure further includes a plurality of parameters relating to how at least one of the one or more first-level operations or at least one of the one or more second-level operations is to be reified by the gene manufacturing system; and the factory order includes information concerning the plurality of parameters.

4. The method of claim 3, wherein the plurality of parameters includes: a first parameter to be used by the gene manufacturing system in the reification of a first second-level operation of the one or more second-level operations, and a second parameter, different from the first parameter and representing the same category of parameters as the first parameter, to be used by the gene manufacturing system in the reification of a second second-level operation of the one or more second-level operations.

5. The method of claim 4, wherein the first parameter indicates a first assembly method, and the second parameter indicates a second, different assembly method.

6. The method of claim 4, wherein the first parameter indicates a first sequence part source and the second parameter indicates a second, different sequence part source.

7. The method of claim 4, wherein the first parameter indicates a first primer source and the second parameter indicates a second, different primer source.

8. The method of claim 1, wherein the data structure includes one or more second-level sequence specifications, each second-level sequence specification includes the one or more second-level operations, and generating a factory order comprises selecting for execution a subset of second-level sequence specifications from the one or more second-level sequence specifications.

9. The method of claim 8, wherein selecting second-level sequence specifications is based upon random selection.

10. The method of claim 8, wherein selecting the subset of second-level sequence specifications is based upon weighting of the second-level sequence operands.

11. The method of claim 8, wherein the second-level sequence specifications are weighted for execution based upon their association with phenotypic properties of nucleotide sequences assembled as a result of at least one prior factory order generated before the factory order.

12. The method of claim 8, wherein the one or more first-level operations are not top-level operations in the data structure.

13. The method of claim 1, wherein a first of the first-level operations includes a cross product operation or a dot product operation, and a first of the second-level operations includes a cross product operation or a dot product operation.

14. The method of claim 1, wherein a first of the first-level operations operates on a plurality of first-level sequence operands and includes a first function modified by a function modifier representing a cross product or a dot product, and a first of the second-level operations operates on a plurality of second-level sequence operands and includes a second function modified by a function modifier representing a cross product or a dot product.

15. The method of claim 14, wherein the first function is a replace function and the second function is a location-resolution function.

16. The method of claim 1, wherein: a given first-level operation of the one or more first-level operations is a replace operation; a given second-level operation of the one or more second-level operations is a location-resolution operation; a given first-level sequence operand of the one or more first-level sequence operands is the first sequence operand; evaluating the expression comprises creating a sequence specification that represents replacing replaceable regions of the plurality of nucleotide sequence parts represented by the first sequence operand with at least one replacement sequence part represented by the second sequence operand; the first sequence operand is a sequence specification including the location-resolution operation; and the execution of the first sequence operand identifies the replaceable regions.

17. The method of claim 16, wherein the plurality of nucleotide sequence parts represented by the first sequence operand are promoter-gene sequences, the replaceable regions are promoters, and the at least one replacement sequence part is at least one promoter other than the promoter it is replacing.

18. The method of claim 1, wherein the first-level sequence operand is expressed as a sequence specification indicating at least one operation to be performed on a plurality of sequence parts.

19. The method of claim 1, wherein the first sequence operand is expressed as a sequence specification or a sequence component, and the second sequence operand is expressed as a sequence specification or a sequence component, wherein each sequence component represents the structure of at least one sequence part without representing any operations to be performed on the at least one sequence part.

20. The method of claim 1, wherein the one or more first-level operations relies on multiple instances of the value resolved by execution of one of the one or more second-level operations, the method further comprising caching the one or more values resolved by execution of the one of the one or more second-level operations to avoid re-execution of the one of the one or more second-level operations.

21. The method of claim 1, wherein the sequence specification represents a plasmid.

22. The method of claim 1, wherein the sequence specification represents a microbe strain sequence.

23. The method of claim 1, wherein the one or more first-level operations or the one or more second-level operations is a concatenation operation, and evaluating the expression comprises generating a sequence specification that represents cross-product concatenation of a plurality of first sequence parts represented by the first operand with one or more second sequence parts represented by the second operand.

24. The method of claim 23, wherein the plurality of first sequence parts are promoters, and the one or more second sequence parts are genes.

25. A system for controlling production of engineered host cells, the system comprising:
one or more processors; and one or more memories operatively coupled to at least one of the one or more processors and having instructions stored thereon that, when executed by at least one of the one or more processors, cause the system to:
(i) receive an expression indicating an operation on a first sequence operand and a second sequence operand, wherein sequence operands represent nucleotide sequence parts, the first sequence operand represents a plurality of nucleotide sequence parts, and the second sequence operand represents at least one nucleotide sequence part;
(ii) evaluate the expression to a sequence specification, wherein the sequence specification comprises a data structure representing (a) the first and second sequence operands, (b) one or more first-level operations to be performed on one or more first-level sequence operands, and (c) one or more second-level operations, the execution of at least one of which resolves a plurality of values of at least one of the one or more first-level sequence operands, wherein the sequence specification represents genetic modifications; and
(iii) generate a factory order based upon execution of one or more of the first-level operations and one or more of the second-level operations, wherein:
(iv) assembly of nucleotide sequence parts into a plurality of nucleotide sequences is based upon the factory order; and
(v) production of a plurality of engineered host cells is based upon introduction of the plurality of nucleotide sequences into a plurality of host cells having a plurality of phenotypes that are based upon the genetic modifications represented by the sequence specification.

26. The system of claim 25, wherein:
selection of a subset of the plurality of engineered host cells is based on assayed phenotypic performance of the plurality of engineered host cells within the subset;
selection of genetic modifications is based on correlations between genetic modifications represented in the sequence specification and assayed phenotypic performance of engineered host cells;
assembly of a second plurality of nucleotide sequences is based upon performing (i)-(iv) with the first and second sequence operands, the one or more first-level operations, and the one or more second-level operations being based on the selected gene modifications; and
production of a second plurality of engineered host cells is based upon introduction of the second plurality of nucleotide sequences into the subset of engineered host cells.

27. The system of claim 25, wherein: the data structure further includes a plurality of parameters relating to how at least one of the one or more first-level operations or at least one of the one or more second-level operations is to be reified by the gene manufacturing system; and the factory order includes information concerning the plurality of parameters.

28. The system of claim 27, wherein the plurality of parameters includes: a first parameter to be used by the gene manufacturing system in the reification of a first second-level operation of the one or more second-level operations, and a second parameter, different from the first parameter and representing the same category of parameters as the first parameter, to be used by the gene manufacturing system in the reification of a second second-level operation of the one or more second-level operations.

29. The system of claim 28, wherein the first parameter indicates a first assembly method, and the second parameter indicates a second, different assembly method.

30. The system of claim 28, wherein the first parameter indicates a first sequence part source and the second parameter indicates a second, different sequence part source.

31. The system of claim 28, wherein the first parameter indicates a first primer source and the second parameter indicates a second, different primer source.

32. The system of claim 25, wherein the data structure includes one or more second-level sequence specifications, each second-level sequence specification includes the one or more second-level operations, and generating a factory order comprises selecting for execution a subset of second-level sequence specifications from the one or more second-level sequence specifications.

33. The system of claim 32, wherein selecting the subset of second-level sequence specifications is based upon random selection.

34. The system of claim 32, wherein selecting the subset of second-level sequence specifications is based upon weighting of the second-level sequence operands.

35. The system of claim 32, wherein the second-level sequence specifications are weighted for execution based upon their association with phenotypic properties of nucleotide sequences assembled as a result of at least one prior factory order generated before the factory order.

36. The system of claim 32, wherein the one or more first-level operations are not top-level operations in the data structure.

37. The system of claim 25, wherein a first of the first-level operations includes a cross product operation or a dot product operation, and a first of the second-level operations includes a cross product operation or a dot product operation.

38. The system of claim 25, wherein a first of the first-level operations operates on a plurality of first-level sequence operands and includes a first function modified by a function modifier representing a cross product or a dot product, and a first of the second-level operations operates on a plurality of second-level sequence operands and includes a second function modified by a function modifier representing a cross product or a dot product.

39. The system of claim 38, wherein the first function is a replace function and the second function is a location-resolution function.

40. The system of claim 25, wherein: a given first-level operation of the one or more first-level operations is a replace operation; a given second-level operation of the one or more second-level operations is a location-resolution operation; a given first-level sequence operand of the one or more first-level sequence operands is the first sequence operand; evaluating the expression comprises creating a sequence specification that represents replacing replaceable regions of the plurality of nucleotide sequence parts represented by the first sequence operand with at least one replacement sequence part represented by the second sequence operand; the first sequence operand is a sequence specification including the location-resolution operation; and the execution of the first sequence operand identifies the replaceable regions.

41. The system of claim 40, wherein the plurality of nucleotide sequence parts represented by the first sequence operand are promoter-gene sequences, the replaceable regions are promoters, and the at least one replacement sequence part is at least one promoter other than the promoter it is replacing.

42. The system of claim 25, wherein the first-level sequence operand is expressed as a sequence specification indicating at least one operation to be performed on a plurality of sequence parts.

43. The system of claim 25, wherein the first sequence operand is expressed as a sequence specification or a sequence component, and the second sequence operand is expressed as a sequence specification or a sequence component, wherein each sequence component represents the structure of at least one sequence part without representing any operations to be performed on the at least one sequence part.

44. The system of claim 25, wherein the one or more first-level operations relies on multiple instances of the value resolved by execution of one of the one or more second-level operations, and the stored instructions further comprise instructions that, when executed, cache the one or more values resolved by execution of the one of the one or more second-level operations to avoid re-execution of the one of the one or more second-level operations.

45. The system of claim 25, wherein the sequence specification represents a plasmid.

46. The system of claim 25, wherein the sequence specification represents a microbe strain sequence.

47. The system of claim 25, wherein the one or more first-level operations or the one or more second-level operations is a concatenation operation, and evaluating the expression comprises generating a sequence specification that represents cross-product concatenation of a plurality of first sequence parts represented by the first operand with one or more second sequence parts represented by the second operand.

48. The system of claim 47, wherein the plurality of first sequence parts are promoters, and the one or more second sequence parts are genes.

49. One or more computer readable media storing instructions for controlling production of engineered host cells, wherein the instructions, when executed, by one or more computing devices, cause at least one of the one or more computing devices to:
(i) receive an expression indicating an operation on a first sequence operand and a second sequence operand, wherein sequence operands represent nucleotide sequence parts, the first sequence operand represents a plurality of nucleotide sequence parts, and the second sequence operand represents at least one nucleotide sequence part;
(ii) evaluate the expression to a sequence specification, wherein the sequence specification comprises a data structure representing (a) the first and second sequence operands, (b) one or more first-level operations to be performed on one or more first-level sequence operands, and (c) one or more second-level operations, the execution of at least one of which resolves a plurality of values of at least one of the one or more first-level sequence operands, wherein the sequence specification represents genetic modifications; and
(iii) generate a factory order based upon execution of one or more of the first-level operations and one or more of the second-level operations, wherein:
(iv) assembly of nucleotide sequence parts into a plurality of nucleotide sequences is based upon the factory order; and
(v) production of a plurality of engineered host cells is based upon introduction of the plurality of nucleotide sequences into a plurality of host cells having a plurality of phenotypes that are based upon the genetic modifications represented by the sequence specification.

50. The one or more computer readable media of claim 49, wherein
selection of a subset of the plurality of engineered host cells is based on assayed phenotypic performance of the plurality of engineered host cells within the subset;
selection of genetic modifications is based on correlations between genetic modifications represented in the sequence specification and assayed phenotypic performance of engineered host cells;
assembly of a second plurality of nucleotide sequences is based upon performing (i)-(iv) with the first and second sequence operands, the one or more first-level operations, and the one or more second-level operations being based on the selected gene modifications; and
production of a second plurality of engineered host cells is based upon introduction of the second plurality of nucleotide sequences into the subset of engineered host cells.

51. The one or more computer readable media of claim 49, wherein: the data structure further includes a plurality of parameters relating to how at least one of the one or more first-level operations or at least one of the one or more second-level operations is to be reified by the gene manufacturing system; and the factory order includes information concerning the plurality of parameters.

52. The one or more computer readable media of claim 51, wherein the plurality of parameters includes: a first parameter to be used by the gene manufacturing system in the reification of a first second-level operation of the one or more second-level operations, and a second parameter, different from the first parameter and representing the same category of parameters as the first parameter, to be used by the gene manufacturing system in the reification of a second second-level operation of the one or more second-level operations.

53. The one or more computer readable media of claim 52, wherein the first parameter indicates a first assembly method, and the second parameter indicates a second, different assembly method.

54. The one or more computer readable media of claim 52, wherein the first parameter indicates a first sequence part source and the second parameter indicates a second, different sequence part source.

55. The one or more computer readable media of claim 52, wherein the first parameter indicates a first primer source and the second parameter indicates a second, different primer source.

56. The one or more computer readable media of claim 49, wherein the data structure includes one or more second-level sequence specifications, each second-level sequence specification includes the one or more second-level operations, and generating a factory order comprises selecting for execution a subset of second-level sequence specifications from the one or more second-level sequence specifications.

57. The one or more computer readable media of claim 56, wherein selecting the subset of second-level sequence specifications is based upon random selection.

58. The one or more computer readable media of claim 56, wherein selecting the subset of second-level sequence specifications is based upon weighting of the second-level sequence operands.

59. The one or more computer readable media of claim 56, wherein the second-level sequence specifications are weighted for execution based upon their association with phenotypic properties of nucleotide sequences assembled as a result of at least one prior factory order generated before the factory order.

60. The one or more computer readable media of claim 56, wherein the one or more first-level operations are not top-level operations in the data structure.

61. The one or more computer readable media of claim 49, wherein a first of the first-level operations includes a cross product operation or a dot product operation, and a first of the second-level operations includes a cross product operation or a dot product operation.

62. The one or more computer readable media of claim 49, wherein a first of the first-level operations operates on a plurality of first-level sequence operands and includes a first function modified by a function modifier representing a cross product or a dot product, and a first of the second-level operations operates on a plurality of second-level sequence operands and includes a second function modified by a function modifier representing a cross product or a dot product.

63. The one or more computer readable media of claim 62, wherein the first function is a replace function and the second function is a location-resolution function.

64. The one or more computer readable media of claim 49, wherein: a given first-level operation of the one or more first-level operations is a replace operation; a given second-level operation of the one or more second-level operations is a location-resolution operation; a given first-level sequence operand of the one or more first-level sequence operands is the first sequence operand; evaluating the expression comprises creating a sequence specification that represents replacing replaceable regions of the plurality of nucleotide sequence parts represented by the first sequence operand with at least one replacement sequence part represented by the second sequence operand; the first sequence operand is a sequence specification including the location-resolution operation; and the execution of the first sequence operand identifies the replaceable regions.

65. The one or more computer readable media of claim 64, wherein the plurality of nucleotide sequence parts represented by the first sequence operand are promoter-gene sequences, the replaceable regions are promoters, and the at least one replacement sequence part is at least one promoter other than the promoter it is replacing.

66. The one or more computer readable media of claim 49, wherein the first-level sequence operand is expressed as a sequence specification indicating at least one operation to be performed on a plurality of sequence parts.

67. The one or more computer readable media of claim 49, wherein the first sequence operand is expressed as a sequence specification or a sequence component, and the second sequence operand is expressed as a sequence specification or a sequence component, wherein each sequence component represents the structure of at least one sequence part without representing any operations to be performed on the at least one sequence part.

68. The one or more computer readable media of claim 49, wherein the one or more first-level operations relies on multiple instances of the value resolved by execution of one of the one or more second-level operations, and the stored instructions further comprise instructions that, when executed, cache the one or more values resolved by execution of the one of the one or more second-level operations to avoid re-execution of the one of the one or more second-level operations.

69. The one or more computer readable media of claim 49, wherein the sequence specification represents a plasmid.

70. The one or more computer readable media of claim 49, wherein the sequence specification represents a microbe strain sequence.

71. The one or more computer readable media of claim 49, wherein the one or more first-level operations or the one or more second-level operations is a concatenation operation, and evaluating the expression comprises generating a sequence specification that represents cross-product concatenation of a plurality of first sequence parts represented by the first operand with one or more second sequence parts represented by the second operand.

72. The one or more computer readable media of claim 71, wherein the plurality of first sequence parts are promoters, and the one or more second sequence parts are genes.

73. The method of claim 1, wherein at least one of the one or more first-level operands is represented as a data structure that represents one or more second-level operations to be performed on one or more second-level operands.

74. The system of claim 25, wherein at least one of the one or more first-level operands is represented as a data structure that represents one or more second-level operations to be performed on one or more second-level operands.

75. The one or more computer readable media of claim 49, wherein at least one of the one or more first-level operands is represented as a data structure that represents one or more second-level operations to be performed on one or more second-level operands.

76. The method of claim 1, wherein the plurality of nucleotide sequences comprises more than one hundred nucleotide sequences.

77. The method of claim 1, wherein the plurality of nucleotide sequences comprises more than one thousand nucleotide sequences.

78. The system of claim 25, wherein the plurality of nucleotide sequences comprises more than one hundred nucleotide sequences.

79. The system of claim 25, wherein the plurality of nucleotide sequences comprises more than one thousand nucleotide sequences.

80. The one or more computer readable media of claim 49, wherein the plurality of nucleotide sequences comprises more than one hundred nucleotide sequences.

81. The one or more computer readable media of claim 49, wherein the plurality of nucleotide sequences comprises more than one thousand nucleotide sequences.

\* \* \* \* \*

SEQUENCE LISTING

<160> NUMBER OF SEQ ID NOS: 19

<210> SEQ ID NO 1

-continued

```
<211> LENGTH: 10
<212> TYPE: DNA
<213> ORGANISM: Artificial Sequence
<220> FEATURE:
<223> OTHER INFORMATION: Unknown biological significance

<400> SEQUENCE: 1
aaattccagg                                                                  10

<210> SEQ ID NO 2
<211> LENGTH: 10
<212> TYPE: DNA
<213> ORGANISM: Artificial Sequence
<220> FEATURE:
<223> OTHER INFORMATION: Unknown biological significance

<400> SEQUENCE: 2
aaattcccgg                                                                  10

<210> SEQ ID NO 3
<211> LENGTH: 10
<212> TYPE: DNA
<213> ORGANISM: Artificial Sequence
<220> FEATURE:
<223> OTHER INFORMATION: Unknown biological significance

<400> SEQUENCE: 3
aaattccggg                                                                  10

<210> SEQ ID NO 4
<211> LENGTH: 10
<212> TYPE: DNA
<213> ORGANISM: Artificial Sequence
<220> FEATURE:
<223> OTHER INFORMATION: Unknown biological significance

<400> SEQUENCE: 4
aaattcctgg                                                                  10

<210> SEQ ID NO 5
<211> LENGTH: 10
<212> TYPE: DNA
<213> ORGANISM: Artificial Sequence
<220> FEATURE:
<223> OTHER INFORMATION: Unknown biological significance

<400> SEQUENCE: 5
aagttccagg                                                                  10

<210> SEQ ID NO 6
<211> LENGTH: 10
<212> TYPE: DNA
<213> ORGANISM: Artificial Sequence
<220> FEATURE:
<223> OTHER INFORMATION: Unknown biological significance

<400> SEQUENCE: 6
aagttcccgg                                                                  10

<210> SEQ ID NO 7
<211> LENGTH: 10
<212> TYPE: DNA
<213> ORGANISM: Artificial Sequence
<220> FEATURE:
<223> OTHER INFORMATION: Unknown biological significance

<400> SEQUENCE: 7
```
aagttccggg                                              10

<210> SEQ ID NO 8
<211> LENGTH: 10
<212> TYPE: DNA
<213> ORGANISM: Artificial Sequence
<220> FEATURE:
<223> OTHER INFORMATION: Unknown biological significance

<400> SEQUENCE: 8
aagttcctgg                                              10

<210> SEQ ID NO 9
<211> LENGTH: 10
<212> TYPE: DNA
<213> ORGANISM: Artificial Sequence
<220> FEATURE:
<223> OTHER INFORMATION: Unknown biological significance

<400> SEQUENCE: 9
aatttccagg                                              10

<210> SEQ ID NO 10
<211> LENGTH: 10
<212> TYPE: DNA
<213> ORGANISM: Artificial Sequence
<220> FEATURE:
<223> OTHER INFORMATION: Unknown biological significance

<400> SEQUENCE: 10
aatttcccgg                                              10

<210> SEQ ID NO 11
<211> LENGTH: 10
<212> TYPE: DNA
<213> ORGANISM: Artificial Sequence
<220> FEATURE:
<223> OTHER INFORMATION: Unknown biological significance

<400> SEQUENCE: 11
aatttccggg                                              10

<210> SEQ ID NO 12
<211> LENGTH: 10
<212> TYPE: DNA
<213> ORGANISM: Artificial Sequence
<220> FEATURE:
<223> OTHER INFORMATION: Unknown biological significance

<400> SEQUENCE: 12
aatttcctgg                                              10

<210> SEQ ID NO 13
<211> LENGTH: 10
<212> TYPE: DNA
<213> ORGANISM: Artificial Sequence
<220> FEATURE:
<223> OTHER INFORMATION: Unknown biological significance

<400> SEQUENCE: 13
aacttccagg                                              10

<210> SEQ ID NO 14
<211> LENGTH: 10
<212> TYPE: DNA

```
<213> ORGANISM: Artificial Sequence
<220> FEATURE:
<223> OTHER INFORMATION: Unknown biological significance

<400> SEQUENCE: 14
aacttcccgg                                                              10

<210> SEQ ID NO 15
<211> LENGTH: 10
<212> TYPE: DNA
<213> ORGANISM: Artificial Sequence
<220> FEATURE:
<223> OTHER INFORMATION: Unknown biological significance

<400> SEQUENCE: 15
aacttccggg                                                              10

<210> SEQ ID NO 16
<211> LENGTH: 10
<212> TYPE: DNA
<213> ORGANISM: Artificial Sequence
<220> FEATURE:
<223> OTHER INFORMATION: Unknown biological significance

<400> SEQUENCE: 16
aacttcctgg                                                              10

<210> SEQ ID NO 17
<211> LENGTH: 19
<212> TYPE: DNA
<213> ORGANISM: Artificial Sequence
<220> FEATURE:
<223> OTHER INFORMATION: Unknown biological significance

<400> SEQUENCE: 17
tcgacgtgac tagctacgt                                                    19

<210> SEQ ID NO 18
<211> LENGTH: 31
<212> TYPE: DNA
<213> ORGANISM: Artificial Sequence
<220> FEATURE:
<223> OTHER INFORMATION: Unknown biological significance

<400> SEQUENCE: 18
gtcagacgta gactgactga tcgacgatca g                                      31

<210> SEQ ID NO 19
<211> LENGTH: 10
<212> TYPE: DNA
<213> ORGANISM: Artificial Sequence
<220> FEATURE:
<223> OTHER INFORMATION: Unknown biological significance

<400> SEQUENCE: 19
agctgagtca                                                              10
```